US005948644A

United States Patent [19]
Dopheide et al.

[11] Patent Number: 5,948,644
[45] Date of Patent: Sep. 7, 1999

[54] POLYNUCLEOTIDES ENCODING EXCRETORY/SECRETORY PROTEINS OF PARASITIC NEMATODES, HOST CELLS TRANSFORMED THEREWITH

[75] Inventors: Theodorus Antonius Aloisius Dopheide, Eltham; Maurice Joseph Frenkel, South Caulfield; Warwick Norman Grant, Armidale; Keith William Savin, South Caufield; Barry M. Wagland, Carlingford, all of Australia

[73] Assignees: Biotechnology Australia Pty Ltd., Roseville; Commonwealth Scientific & Industrial Research Org., Campbell, both of Australia

[21] Appl. No.: 08/467,046

[22] Filed: Jun. 6, 1995

Related U.S. Application Data

[62] Division of application No. 08/261,207, Jun. 15, 1994, abandoned, which is a continuation of application No. 07/904,055, Jun. 26, 1992, abandoned, which is a continuation-in-part of application No. 07/548,901, filed as application No. PCT/AU89/00416, Sep. 26, 1989, abandoned.

[30] Foreign Application Priority Data

Sep. 26, 1988 [AU] Australia ................................. PJ0621
Sep. 26, 1988 [AU] Australia ................................. PJ0622
Sep. 26, 1988 [AU] Australia ................................. PJ0623
Sep. 26, 1988 [AU] Australia ................................. PJ0624

[51] Int. Cl.$^6$ ............................. C12P 21/06; C12N 5/00; C07H 21/02; C07K 1/00
[52] U.S. Cl. ................ 435/69.3; 435/252.3; 435/254.11; 435/254.2; 435/325; 435/320.1; 435/419; 536/23.1; 536/23.4; 536/23.5; 530/300; 530/350; 424/184.1; 424/265.1; 424/266.1
[58] Field of Search .................................. 536/23.1, 23.4, 536/23.5; 435/252.3, 240.2, 254.11, 240.4, 254.2, 325, 419, 69.3, 320.1; 530/300, 350; 424/184.1, 265.1, 266.1

[56] References Cited

U.S. PATENT DOCUMENTS 4,879,213  11/1989  Fox et al. .

FOREIGN PATENT DOCUMENTS

| 247354 | 2/1961 | Australia . |
|---|---|---|
| B-36095/24 | 6/1985 | Australia . |
| A-76729/87 | 2/1988 | Australia . |
| A-15845/88 | 11/1988 | Australia . |
| 894603 | 8/1960 | United Kingdom . |
| WO 87/06590 | 11/1987 | WIPO . |
| WO 88/00835 | 2/1988 | WIPO . |
| WO 88/00239 | 1/1989 | WIPO . |
| WO 89/00163 | 1/1989 | WIPO . |

OTHER PUBLICATIONS

Chemical Abstracts, 81(13) (1974) Abstract No. 76156y.
Chemical Abstracts, 99(17) (1983) Abstract No. 137907q.
Biological Abstracts, 80 Abstract No. 61135.
Chemical Abstracts, 107(17) (1985) Abstract No. 149890a.
*The J. of Immun.*, 132:898–904, 1984.
*Journal of Parasitology*, 67:592–593 (1981).
*Molecul. & Biochem. Parasitology*, 31:35–46 (1988).
*Immunology*, 58:515–522 (1986).
*The Jour. of Parasitology*, 48:562–571 (1962).
*Reviews in Rural Science*, 6:67–74 (1984).
"The Role of Immunologically Specific and Non–Specific Components of Resistance in Cross–Protection . . . ", *Int. J. for Parasitol.*, 7: 211–215 (1977).
"Failure to Vaccinate Lambs Against Haemonchus Contortus With Functional Metabolic Antigens . . . ", *Int. J. for Parasitol.*, 5: 427–430 (1975).
"Immunoregulation of Parasites in Natural Host–Parasite Systems . . . ", *Biology and Control of Endoparasites* pp. 297–323 (1982).
"Vaccination Against the Nematode *Trichostrongylus Colubriformis* 1. Vaccinations of Guinea–pigs With Worm Homogenates & Soluble Products . . . ", *Int. J. Parasitol.*, 4: 293–299 (1974).
"Vaccination Against the Nematode *Trichostrongylus Colubriformis* III. Some Observations on Factors Influencing Immunity to Infection in Vaccinated Guinea–pigs", *Int. J. Parasitol.*, 8: 33–37 (1978).
"Immune Expulsion of Parasitic Nematodes from the Alimentary Tract", *Int. J. Parasitol.*, 19(2): 139–168 (1989).
"Attempts to Probe the Antigens and Protective Immunogens of *Trichostrongylus Colubriformis* In Immunoblots With Sera From Infected And Hyperimmune Sheep . . . ", *Int. J. Parasitol.*, 15(2): 129–136 (1985).
"Partial Protection of Lambs Against *Haemonchus contortus* by Vaccination With A Fractionated Preparation of the Parasite", *Vet. Parasitol.*, 23: 211–221 (1987).
"*Oesophagostomum Radiatum:* Successful Vaccination of Calves with High Molecular Weight Antigens", *Int. J. Parasitol.*, 19(3): 271–274 (1989).

(List continued on next page.)

*Primary Examiner*—Anthony C. Caputa
*Assistant Examiner*—Mark Navarro
*Attorney, Agent, or Firm*—Foley & Lardner

[57] ABSTRACT

The invention provides excretory/secretory antigens derived from parasitic nematode species which are capable of inducing protective immunity against infection by parasitic nematode species, and related antigenic molecules. The invention also provides nucleotide sequences encoding the antigens and related molecules of the invention, recombinant DNA molecules comprising the nucleotide sequences, and transformed hosts carrying the recombinant DNA molecules. The invention further provides antibodies against the antigens and related molecules, and antibody compositions comprising the antibodies, vaccines comprising the antigens and/or related molecules and methods of treating or preventing nematode infections using the antigens and related molecules, vaccines, antibodies and/or antibody compositions of the invention.

29 Claims, 1 Drawing Sheet

OTHER PUBLICATIONS

"Vaccination of Young Lambs by Means of a Protein Fraction Extracted from Adult *Haemonchus contortus*", *Parasitology*, 94: 385–397 (1987).

"Comparision of the Kinetics of Expulsion of *Trichostrongylus colubriformis* from Previously Uninfected, Reinfected, and Vaccinated Guinea Pigs", *J. Parasitol.*, 63(4) 761–762 (1977).

"Immunity in the Guinea–pig to *Trichostrongylus colubriformis*–an Experimental System for the Study of Immunity", *Parasitology*, 55: 10P, 1965.

"Isolation, cDNA Cloning and Characterization of a 30KD Host–protective Antigen Secreted By The Sheep Parasite *Trichostrongylus Colubriformis*", *Vaccines '88*, G66 (1988).

Localization and Species Distribution of a 31 Kilodalton Glycoprotein Antigen (GP31) Of *Ostertagia Circumcincta*, *Australian Society for Parasitol.*, Sydney Sep. 27–30 Program, 45, 1988.

"Isolation and Characterization of a Proteolytic Enzyme from the Adult Hookworm *Ancylostoma Caninum*", *J. Biol. Chem.*, 260(12): 7343–7348 (1985).

A λgt11 cDNA Recombinant that Encodes *Dirofilaria Immitis* Paramyosin, *Mol. Biochem. Parasitol.*, 35: 31–42 (1989).

"Molecular Cloning of an Immunodominant Antigen of *Onchocerca Volvulus*", *J. Exp. Med.*, 168: 1199–1204 (1988).

"Construction of *Onchocerca Volvulus* cDNA Libraries and Partial Characterization of the cDNA for a Major Antigen", *Mol. and Biochem. Parasitol.*, 34: 241–250 (1988).

"Cloning and Characterization of a Potentially Protective Antigen in Lymphatic Filariasis", *Proc. Natl. Acad. Sci. USA*, 85: 3604–3607 (1988).

"Attempts to Probe the Antigens and Protective Immunogens of *Trichostongylus Colubriformis* In Immunoblots With Sera . . . ", *Int. J. Parasitol.*, 15(2) 129–136 (1985).

"Cloning in Single–stranded Bacteriophage as an Aid to Rapid DNA Sequencing", *J. Mol. Biol.*, 143: 161–178 (1980).

"Versatile Cassettes Designed for the Copper Inducible Expression of Proteins in Yeast", *Plasmid*, 21: 147–150 (1989).

"Screening λgt Recombinant Clones by Hybridization to Single Plaques in situ", *Science*, 196: 180–182 (1977).

"Directed Deletion of a Yeast Transfer RNA Intervening Sequence", *Science*, 209: 1396–1400 (1980).

"Nucleotide Sequence Analysis of the Complement Resistance Gene from Plasmid R100", *J. Bacteriology*, 151(2): 819–827 (1982).

"Plasmid vectors for high–efficiency expression controlled by the pl promoter of coligphage lambda", *Gene*, 15: 81–93 (1981).

"The Murine Plasma Cell Antigen PC–1: Purification and Partial Amino Acid Sequence", *J. Immunology*, 134(1): 443–448 (1985).

"Effects on *Trichinella spiralis* of Host Responses to Purified Antigens", *Science*, 227: 948–950 (1985).

"A Search for a Simple Keratin–Fractionation and Peptide Mapping of Proteins from Feather Keratins", *Aust. J. Biol. Sci.*, 26: 401–413 (1973).

"Cleavage of Structural Proteins during the Assembly of the Head of Bacteriophage T4", *Nature*, 227: 680–685 (1970).

"Constructing and Screening cDNA Libraries in λgt10 and λgt11", *DNA Cloning*, 1(2): 49–78 (1985).

"Basis for the Development of Vaccines for Control of Diseases Produced by Metazoan Parasites", *Reviews in Rural Science*, 6: 67–74 (1984).

"A Preliminary Evaluation of Factors Affecting An Experimental System for Vaccination–And–Challenge With *Haemonchus Contortus* In Sheep", *Int. J. Parasitol.*, 19(2): 169–175 (1989).

"Shared Carbohydrate Epitopes on Distinct Surface and Secreted Antigens of the Parasitic Nematode *Toxocara canis*", *J. Immunology*, 139(1): 207–214 (1987).

"Mice Vaccinated against *Nematospiroides dubius* with Antigens Isolated by Affinity Chromatography From Adult Worms", *Immunol. Cell. Biol.*, 65(3): 223–230 (1987).

"Glycoconjugate Antigens from Parasitic Nematodes", *Molecular Paradigms for Eradicating Helminthic Parasites.* UCLA Symposia vol. 60 (McInnes AJ ed) A.R. Liss Publication, New York 1987, pp. 267–279.

"Nematode Antigens", *Current Topics in Microbiol. and Immonol.*, 120: 173–203 (1985).

*Int. J. for Parasitology*, 15:129–136 (1985).

Bas et al. (1986) JBC vol. 261, No. 2, 817–827.

O'Donnell et al. (1989) Int. J. Parasitol. vol. 19(3), 327–335.

Burgess et al. (1990) J. Cell. Biol. vol. 111, 2129–2138.

Lazar et al. (1988) Mol. Cell. Biol., 1247–1252.

Fig. 1

Structure of TraT-TcAdESA1 fusion

4525,

TraT Signal sequence
ATG.AAA.ATG.AAA.AAA.TTG.ATG.ATG.GTT.GCA.CTG.GTC.AGT.TCC.ACT.CTG.GCC.CTT.TCA.GGG.
Met Lys Met Lys Lys Leu Met Met Val Ala Leu Val Ser Ser Thr Leu Ala Leu Ser Gly TraT N-terminus                                    Linker sequences
TGT.GGT.GCG.ATG.AGC.ACA.GCA.ATC.AAG.AAG.CAG.AAT.TCG.AGC.TCG.GTA.CAA.TTC.GGG.
Cys Gly Ala Met Ser Thr Ala Ile Lys Lys Gln Asn Ser Ser Val Gln Phe Gly Old Pvu2 site Construct Old Xmn1 site
                          Junction N-terminus, Mature TcAdESA1 Complete TcAdESA1 sequence 3092, cl   TcAdESA1
GGC.AAC.ACT.TAC.AGT.GCA.AAC.AAT.AAG.CAA.CAG
Gly Asn Thr Tyr Ser Ala Asn Asn Lys Gln Gln

POLYNUCLEOTIDES ENCODING EXCRETORY/SECRETORY PROTEINS OF PARASITIC NEMATODES, HOST CELLS TRANSFORMED THEREWITH

This application is a divisional of application Ser. No. 08/261,207, filed Jun. 15, 1994, now abandoned; which is a continuation of application Ser. No. 07/904,055 filed Jun. 26, 1992, now abandoned; which is a continuation-in-part of application Ser. No. 07/548,901 filed Jul. 26, 1990, now abandoned, which is the U.S. national phase of international patent application Ser. No. PCT/AU89/00416 filed Sep. 26, 1989.

TECHNICAL FIELD

The invention relates to the identification of antigens which induce protective immunity in a host against infection by parasitic nematode species, such as species of the genera Trichinella, Ancylostoma, Strongylus, Trichostrongylus, Haemonchus, Ostertagia, Ascaris, Toxascaris, Uncinaria, Trichuris, Dirofilaria, Toxocara, Necator, Enterobius, Strongyloides and Wuchereria, especially the genera Trichostrongylus and Haemonchus. Examples of such species include *Trichinella spiralis, Ancylostoma caninum, Strongylus vulgaris, Trichostrongylus colubriformis, Haemonchus contortus, Ostertagia ostertagi, Ascaris suum, Toxascaris leonina, Uncinaria stenocephala, Trichuris vulpis, Dirofilaria immitis*, the larvae of Toxocara spp., *Necator americanus, Ancylostoma duodenale, Ascaris lumbricoides, Trichuris trichiura, Enterobius vermicularus, Strongyloides stercoralis* and *Wuchereria bancrofti*, particularly *Trichostrongylus colubriformis* and *Haemonchus contortus*.

The invention also relates to nucleotide sequences encoding these antigens, as well as to recombinant DNA molecules containing such nucleotide sequences and host cells expressing these nucleotide sequences.

The invention further relates to methods for the production of the antigens, nucleotide sequences, recombinant DNA molecules and hosts of the invention.

The invention relates to antibodies raised against the antigens of the invention and to compounds which act in a manner similar to those antibodies.

Additionally, the invention relates to vaccines which induce protective immunity against infection by parasitic nematodes such as species of the genera Trichinella, Ancylostoma, Strongylus, Trichostrongylus, Haemonchus, Ostertagia, Ascaris, Toxascaris, Uncinaria, Trichuris, Dirofilaria, Toxocara, Necator, Enterobius, Strongyloides, and Wuchereria, especially the genera Trichostrongylus and Haemonchus. Examples of such species include *Trichinella spiralis* or *Ancylostoma caninum* in man, *Strongylus vulgaris* in horses, *Trichostrongylus colubriformis* in sheep and goats, *Haemonchus contortus* in sheep and goats, *Ostertagia ostertagi* in cattle, *Ascaris suum* or *Trichinella spiralis* in pigs, *Toxascaris leonina* or *Uncinaria stenocephala* in cats, *Ancylostoma caninum* or *Trichuris vulpis* in dogs, *Dirofilaria immitis* in dogs, or the larvae of Toxocara spp in man, or infection by *Necator americanus, Ancylostoma duodenale, Ascaris lumbricoides, Trichuris trichiura, Enterobius vermicularus, Strongyloides stercoralis* or *Wuchereria bancrofti*, and particularly *Trichostrongylus colubriformis* or *Haemonchus contortus*.

BACKGROUND ART

Nematodes (nema—thread; oides—resembling), which are unsegmented roundworms with elongated, fusiform, or saclike bodies covered with cuticle, are virtually ubiquitous in nature, inhabiting soil, water and plants, and are importantly involved in a wide range of animal and plant parasitic diseases.

The roundworm parasites of mammals belong to the phylum Nemathelminthes. The roundworms include the hookworm (e.g. *Necator americanus* and *Ancylostoma duodenale*), roundworm (e.g. the common roundworm *Ascaris lumbricoides*), whipworm (e.g. *Trichuris trichiura*), and the pinworm or threadworm (e.g. *Enterobius vermicularus*), as well as *Strongyloides stercoralis, Trichinella spiralis* and the filarial worm *Wuchereria bancrofti*. Other important roundworm parasites include *Ancylostoma caninum* (infections of man), *Strongylus vulgaris* (infections of horses), *Trichostrongylus colubriformis, Ostertagia circumcincta* (infections of sheep and goats), *Haemonchus contortus* (infections of sheep and goats), *Ostertagia ostertagi, Haemonchus placei* (infections of cattle), *Ascaris suum* (infections of pigs), *Toxascaris leonina* or *Uncinaria stenocephala* (infections of dogs), Toxocara spp (circulatory infections of man) and *Dirofilaria immitis* (circulatory infections of cats and dogs).

Even when symptom-free, parasitic worm infections are harmful to the host animal for a number of reasons; e.g. they deprive the host of food, injure organs or obstruct ducts, may elaborate substances toxic to the host, and provide a port of entry for other organisms. In other cases, the host may be a species raised for food and the parasite may be transmitted upon eating to infect the ingesting animal. It is highly desirable to eliminate such parasites as soon as they have been discovered.

More commonly, such infections are not symptom-free. Helminth infections of mammals, particularly by parasitic nematodes, are a source of great economic loss, especially of livestock and pets, e.g. sheep, cattle, horses, pigs, goats, dogs, cats, and birds, especially poultry (see CSIRO/BAE Report—"Socio-economic Developments and Trends in the Agricultural Sector: Implications for Future Research"). These animals must be regularly treated with anthelminthic chemicals in order to keep such infections under control, or else the disease may result in anaemia, diarrhoea, dehydration, loss of appetite, and even death.

The only currently available means for controlling helminth infections is with the use of anthelminthic chemicals, but these are only effective against resident worms present at the time of treatment. Therefore, treatment must be continuous since the animals are constantly exposed to infection; e.g. anthelminthic treatment with diethylcarbamazine is required every day or every other day most of the year to control *Dirofilaria immitis* or the dog heartworm. This is an expensive and labour intensive procedure. Due to the widespread use of anthelminthic chemicals, the worms may develop resistance and so new and more potent classes of chemicals must be developed. An alternative approach is clearly desirable.

The development of a vaccine against parasitic. nematodes would overcome many of the drawbacks inherent in chemical treatment for the prevention and curing of helminthic infections. The protection would certainly last longer, only the vaccinated animal would be affected, and the problems of toxicity and persistence of residues would be minimized or avoided. Accordingly, there have been several reported attempts to develop such vaccines using parasitic nematodes; unfortunately, they have met with limited success and factors such as material availability and vaccine stability have precluded their large scale use.

One such attempt described by J. K. Dineen, (1977) involves the use of irradiated larval vaccines. As with other such attempts, the utility of this method is restricted by the requirement to maintain viable nematodes for prolonged periods.

The failure of killed vaccine preparations to afford good anthelminthic protection has been thought to be due to a number of factors. For example, it has been considered by J. T. M. Neilson (1975) that parasitic nematodes may have evolved mechanisms by which they can secrete products which immunosuppress or immunomodulate the host's immune system, thereby both preventing the development of an effective immune response and rendering the host susceptible to other infections. It is believed by Dineen and Wagland (1982), that immunosuppressants or immunomodulators may be present in the crude preparations of parasitic nematodes which are used in the killed vaccines. A second problem suggested by this review article is that parasitic nematodes may have altered their antigen profile to one which resembles that of the host so that, in a natural infection, vigorous immunlogical reactions are not provoked by protective parasitic antigens. Such a phenomenon would also occur following vaccination with impure preparations of killed nematodes or extracts thereof.

Some workers have shown accelerated explusion of worms from host animals using whole homogenates of worms and impure subfractions see for example Rothwell and co-workers (1974, 1977, 1979), O'Donnell et at (1985), Neilson and Van de Walle (1987), Silverman: U.K. Patent 894603, Australian Patent 247 354, Adams (1989), East et al (1989), Munn and Greenwood (1987) (Australian Patent Application No. 77590/87), Connan (1965), Savin et al (1988) and McGillivery et al (1988).

In all of these studies, crude extracts of nematodes have been used to vaccinate animals, and no defined antigen or individual components of the extracts have been identified as being responsible for protection.

There have been some reports attempting to identify purified protective components, see for example Silberstein and Despommier (1985), Hotez et al (1985), Grandea et al (1989), Lucius et al (1988), Donelson et al (1988), Nilsen et al (1988). However, protection has either not been shown or not substantiated for the components described.

In only one natural host/parasitic nematode system has a purified cloned subunit been shown to be protective. In Australian Patent Application No. 19998/88, it was demonstrated that a recombinant DNA derived antigen shown to be nematode tropomyosin, gave 50% protection in sheep against *Haemonchus contortus* challenge. For reasons which will become clear later in this specification, this antigen is different to those identified in the current specification: the current antigens being found in the excretory/secretory fluids of nematodes following incubation in vitro.

The CSIRO/BAE working paper "Socio-economic Developments and Trends in the Agricultural Sector: Implications for Future Research" cited intestinal parasites as one of the three most urgent health problems in the Australian sheep industry and indicated that the development of vaccines holds great promise for better control of these infections.

It is well established that animals which are infected with parasitic nematodes develop an immunity which renders them less susceptible to subsequent infection (see Rothwell 1989 for review).

Although it has been demonstrated (e.g. O'Donnell et al 1985) that many parasite proteins are recognised by the immune system of infected host animals during parasitic infection, many of the immune responses will have no functional significance in terms of resistance to re-infection. The major step is to identify, from the many thousands of proteins present in the parasitic organism, the individual proteins which can induce immune responses in the host animal that protect it from re-infection.

Recent advances in biotechnology and in particular recombinant DNA technology, realistically offer the opportunity to produce commercially-viable vaccines against a range of economically-important parasites of man and domestic animals. This approach would overcome many of the problems proposed to account for the lack of efficacy of killed vaccines using crude parasite preparations. For example, the vaccines produced by recombinant DNA techniques would not contain immunosuppressants or immunomodulators which may be found in crude extracts of parasitic nematode species. But it is necessary to first identify the antigens. Once identified and characterised, recombinant DNA technology could be used to construct microorganisms which synthesize those proteins or portions of the proteins containing protective epitopes and use the products synthesized by the recombinant organism in vaccines to protect animals from infection with the parasites.

The present inventors have studied in detail the excretory/secretory products from adult *T. colubriformis* and components from the mixture which are capable of giving protection following vaccination of target animals have been purified and characterised at the molecular level.

Definitions

The term "adjuvant" as used throughout the specification refers to an agent used in immunising compositions to enhance the immune response of an immunised host to the administered immunising composition.

The term "parenteral" as used herein includes subcutaneous injections, intraperitoneal or intramuscular injections, or infusion techniques.

The term "homologue" refers to proteinaceous molecules or to DNA sequences coding for those proteinaceous molecules which are related in structure to a first proteinaceous molecule or DNA sequence to such an extent that it is clear that the proteinaceous molecules themselves, or as encoded by the DNA, are related. Related DNA sequences are referred to as homologous genes and the related proteins are referred to as homologous antigens. The homology is expected to be at least 70% over 20 amino acids at the amino acid sequence level and at least 50% over 60 nucleotides at the DNA level.

It is recognised that the nematode population worldwide is genetically diverse as is the case for all organisms which reproduce sexually. Each individual of a population differs subtly from the others in the population and these differences are a consequence of differences in the sequence of the DNA which each individual inherits from its parents.

Further, random mutational events which can occur in either sexually or asexually reproducing organisms are a further source of genetic variation.

Thus, for each gene encoding a particular protein, there are likely to be differences in the sequence among the population of individuals.

Such related molecules are referred to herein as homologues.

Further homologous antigens may be defined as antigens related by evolution but not necessarily by function. Similar but not necessarily identical DNA or protein sequences may be provided. It should be noted however that function in this sense relates to the natural in vivo function of the protein.

Illustration of this point is provided by considering:

1. Tc Ad ESA 1–5 from *Trichostrongylus colubriformis* and other nematode species.
2. Tc Ad ESA 1–5 from variants or different individuals of the *T. colubriformis* population.
3. Tc Ad ESA 1–5 and related proteins from nematodes, which are homologues of Tc Ad ESA 1–5 as defined herein.

It is stressed that for the purposes of this invention, the homologues of antigens encompassed include only those molecules which share the immunological function of the antigens as defined herein.

Such homologous molecules may exist in the nematode population worldwide and will be capable, when incorporated into a vaccine either alone or in combination with other antigens, of eliciting in animals vaccinated with those molecules protective immune response.

In the context of this invention, the DNA from *T. colubriformis* which codes for an antigen of the invention can be used in DNA hybridisation experiments to identify specific DNA sequences in other species of parasitic nematodes. The conditions used for the hybridisation experiments will indicate the approximate % homology of the related DNA sequences to the DNA isolated from *T. colubriformis*. Typically, the conditions will be such that the related DNA sequences hybridising to the DNA isolated from *T. colubriformis* are at least 50% homologous in nucleotide sequence. These related DNA segments code for antigens in those other species of parasitic nematodes which are also related in amino acid sequence to the protective antigens isolated from *T. colubriformis*. It is contended that the related proteins will act as effective immunogens to protect animals from parasitism by the other species of parasitic nematodes with the possibility also of cross-species protection. These related DNA sequences are referred to as homologous genes and the related proteins are referred to as homologous antigens. Homologues of the invention may also be generated in vitro as herein described.

The term "derived" in the context of the antigens of the invention as used herein is intended to encompass antigens obtained by isolation from a nematode life stage expressing the antigen, as well as antigens obtained by manipulation of and expression from nucleotide sequences prepared from nematodes, including genomic DNA, mRNA, cDNA synthesized from mRNA and synthetic nucleotides prepared to have sequences corresponding to the antigen encoding sequences.

It is also intended to encompass synthetic peptide antigens prepared on the basis of the known amino acid sequences of the antigens as expressed by nematodes or cell lines expressing recombinant forms of the antigens.

Further, it should be recognised that it is possible to generate molecules which are not related to the Tc Ad ESA 1–5 antigens by evolution or necessarily by structure but which may serve as immunogens to generate an immune response against protective epitopes on the Tc Ad ESA 1–5 antigens and thereby act as effective vaccines. These molecules are referred to herein as "analogues" and, to the extent that they fulfil the functions of immunogens as defined herein, they are included within the scope of the invention. Such analogues include chemically synthesized oligopeptide molecules with sequences corresponding to portions of the amino acid backbone of the Tc Ad ESA 1–5 molecules, oligopeptides which when used as immunogens elicit an immune response which recognises native Tc Ad ESA 1–5 antigens in nematodes, and anti-idiotype antibodies raised against the variable region of antibodies which recognise the epitope(s) of the Tc Ad ESA 1–5 antigens.

Derivatives of antigens of the invention are molecules made from the antigens or molecules which are related to the antigens in a manner which suggests their preparation from the antigens.

DESCRIPTION OF INVENTION

The present inventors have found that protective immunity against infection by parasitic nematodes can be induced by immunization with excretory/secretory products of a parasitic nematode species. Five molecules termed Tc Ad ESA1 (SEQ ID NO: 12), Tc Ad ESA2 (SEQ ID NO: 6), Tc Ad ESA3 (SEQ ID NO: 4), Tc Ad ESA4 (SEQ ID NO: 25) and Tc Ad ESA5 are described which have been purified from the excretory-secretory fluids of mature adults of *T. colubriformis* and characterized. The present inventors have found that on vaccination, these proteins induce protective responses in guinea pigs against infection with *T. colubriformis.*

Adult worms were recovered from sheep 21 days after infection, washed and maintained in RPMI 1640 culture medium, containing antibiotics at 37° C. for 16 hours. This culture medium which contains the excretory/secretory fluids from *T. colubriformis*, was concentrated over Diaflo membranes, and fractionated by adsorption to a lentil lectin-Sepharose 4B column.

The unbound fraction ($LL^-$) and the bound fraction ($LL^+$, eluted with methylmannoside) each contained only a few protein bands and were fractionated further by polyacrylamide gel electrophoresis and electroelution. Three proteins, designated Tc Ad ESA1 (SEQ ID NO: 12), Tc Ad ESA2 (SEQ ID NO: 6) and Tc Ad ESA5 have been isolated from the lentil lectin bound fraction and a further two proteins designated Tc Ad ESA3 (SEQ ID NO: 4) and Tc Ad ESA4 (SEQ ID NO: 25) were isolated from the unbound fraction. All five proteins confer immunity to *T. colubriformis* infection following intraperitoneal injection of guinea pigs, a laboratory model for sheep.

Examples of the antigens of the invention are the purified proteins Tc Ad ESA1 (SEQ ID NO: 12), Tc Ad ESA2 (SEQ ID NO: 6), Tc Ad ESA3 (SEQ ID NO: 4), Tc Ad ESA4 (SEQ ID NO: 25) and Tc Ad ESAS having molecular weights of 30, 37, 17, 11 and 81 kD respectively as estimated by SDS-PAGE.

According to a first embodiment of this invention there is provided an antigen comprising:

an excretory/secretory protein derived from a first parasitic nematode species and capable of inducing protective immunity against infection of a host by a second parasitic nematode species, which may be the same as or different from the first nematode species; or a protein molecule comprising all, part, an analogue, homologue, derivative or combination thereof of the excretory/secretory protein, which protein molecule is capable of inducing protective immunity in a host against infection by a parasitic nematode.

Preferably, the excretory/secretory protein has an approximate molecular weight of 11, 17, 30, 37 or 81 kD as estimated by SDS-PAGE.

Typically, the first parasitic nematode species is selected from species of the genera Trichinella, Ancylostoma, Strongylus, Trichostrongylus, Haemonchus, Ostertagia, Ascaris, Toxascaris, Uncinaria, Trichuris, Dirofilaria, Toxocara, Necator, Enterobius, Strongyloides and Wuchereria. Examples of such species include *Trichinella spiralis, Ancylostoma caninum, Strongylus vulgaris, Trichostrongylus colubriformis, Haemonchus contortus, Ostertagia* ostertagi, Ascaris suum, Toxascaris leonina, Uncinaria stenocephala, Trichuris vulpis, Dirofilaria immitis, Toxocara spp, Necator americanus, Ancylostoma duodenale, Ascaris lumbricoides, Trichuris trichiura, Enterobius vermicularus, Strongyloides stercoralis and Wuchereria bancrofti.

Typically, the second parasitic nematode species is selected from species of the genera Trichinella, Ancylostoma, Strongylus, Trichostrongylus, Haemonchus, Ostertagia, Ascaris, Toxascaris, Uncinaria, Trichuris, Dirofilaria, Toxocara, Necator, Enterobius, Strongyloides and Wuchereria. Examples of such species include *Trichinella spiralis, Ancylostoma caninum, Strongylus vulqaris, Trichostrongylus colubriformis, Haemonchus contortus, Ostertagia ostertagi, Ascaris suum, Toxascaris leonina, Uncinaria stenocephala, Trichuris vulpis, Dirofilaria immitis*, Toxocara spp, *Necator americanus, Ancylostoma duodenale, Ascaris lumbricoides, Trichuris trichiura, Enterobius vermicularus, Strongyloides stercoralis* and *Wuchereria bancrofti*.

Preferably, the first parasitic nematode species is *T. colubriformis*.

Preferably, the second parasitic nematode species is *T. colubriformis* or *H. contortus*.

According to a second embodiment of this invention there is provided: a first nucleotide sequence encoding the amino acid sequence of an antigen of the first embodiment; a nucleotide sequence which hybridizes to the first nucleotide sequence; or a nucleotide related by mutation including single or multiple base substitutions, insertions or deletions to the first nucleotide sequence.

Preferred nucleotide sequences of the invention are those encoding the excretory/secretory proteins of the first embodiment having approximate molecular weights of 11, 17, 30, 37 and 81 kD as estimated by SDS-PAGE.

Preferably, the nucleotide sequence is a DNA sequence. The DNA sequences embraced by the present invention can be prepared, for example, from *T. colubriformis* cells by extracting total DNA therefrom and isolating the sequences by standard techniques. Alternatively, the DNA may be prepared in vitro, synthetically or biosynthetically, such as by the use of an mRNA template.

According to a third embodiment of this invention there is provided a process for selecting a DNA or RNA sequence coding for an antigen according to the first embodiment which process comprises providing one or more DNA or RNA sequences and determining which of the sequences hybridizes with a DNA or RNA sequence known to code for an antigen of the first embodiment or providing an antiserum to the antigen and identifying host-vector combinations that express the antigen.

The sequences may be from natural sources, may be RNA sequences, synthetic sequences, DNA sequences from recombinant DNA molecules or combinations of such sequences.

Preferably, the process used to identify and characterize DNA coding for the antigen involves the extraction of mRNA species from cells producing the antigen, their conversion to double stranded DNA (cDNA) and the insertion of these into an autonomously replicating factor, such as a plasmid or phage vector. This is followed by transformation of a host cell such as a bacterial strain with the factor and screening of the library produced with synthetic DNA probes which are complementary to the antigen encoding mRNA or DNA sequences in order to detect those clones which contain DNA coding for the antigen as opposed to any other cell proteinaceous components.

According to a fourth embodiment of this invention, there is provided a recombinant DNA molecule comprising a DNA sequence of the third embodiment and vector DNA.

The DNA sequence may be a natural, synthetic or biosynthetic DNA sequence.

Preferred recombinant DNA molecules of the invention include an expression control sequence operatively linked to the DNA sequence.

In one preferred form of the invention, the DNA sequence is operatively linked to the β-galactosidase gene of *E. coli*. Other preferred control systems include those of the tryptophan (Trp) operon, the Tra-T gene of *E. coli*, the leftward promoter of bacteriophage lambda, the Cup 1 promoter and hybrid promoters such as tac or viral promoters such as the SV40 early promoter.

Preferably, the vector DNA is plasmid DNA. Suitable plasmid vectors include pUR290, pUC18, pYEUC114 and derivatives thereof.

Alternatively, the vector DNA may be bacteriophage DNA such as bacteriophage lambda and derivatives thereof, such as lambda gt11 and lambda gt10.

According to a fifth embodiment of this invention there is provided a fused gene comprising a promoter, a translation start signal and a DNA sequence of the third embodiment.

According to a sixth embodiment of this invention there is provided a process for the preparation of a recombinant DNA molecule of the fourth embodiment which process comprises providing a DNA insert comprising a DNA sequence of the third embodiment and introducing the DNA insert into a cloning vector.

Preferably, the DNA insert is introduced into the cloning vector in correct spacing and correct reading frame with respect to an expression control sequence.

According to a seventh embodiment of this invention there is provided a transformed host, transformed with at least one recombinant DNA molecule of the fourth embodiment.

Preferably, the transformed host is capable of expressing an antigen of the first embodiment.

Suitable hosts include bacterial cells, yeasts such as *Saccharomyces cerevisiae* strain CL13-ABSY86 , other fungi, vertebrate cells, insects cells, plant cells, human cells, human tissue cells, live viruses such as vaccinia and baculovirus, and whole eukaryotic organisms.

Suitable bacterial hosts include *E. coli* and other enteric organisms, Pseudomonas, and Bacillus species.

Preferred hosts are *E. coli* K12 derivatives; in particular JM109 and Y1090.

According to an eighth embodiment of this invention there is provided a process for transforming a host to provide a transformed host of the seventh embodiment which process comprises providing a host, making the host competent for transformation, and introducing into the host a recombinant DNA molecule of the fourth embodiment.

According to a ninth embodiment of this invention there is provided an expression product of a transformed host of the seventh embodiment which product comprises an antigen of the first embodiment.

Preferably, the expression product is provided in substantially pure form.

Preferably, the expression product comprises a first polypeptide sequence homologous to the host and a second polypeptide sequence which is an amino acid sequence coding for an antigen of the first embodiment.

More preferably, the first amino acid sequence is part or all of β-galactosidase or Tra-T and the host cell is *E. coli*.

According to a tenth embodiment of this invention there is provided a process for the biosynthesis of a proteinaceous product comprising an antigen of the first embodiment which process comprises:

transforming a host with a recombinant DNA molecule of the fourth embodiment so that the host is capable of expressing a proteinaceous product which includes an antigen of the first embodiment; culturing the host to obtain expression; and collecting the proteinaceous product.

According to an eleventh embodiment of this invention there is provided an epitope of an antigen of the first embodiment which is responsible for the protective immune response. The epitope may be created artificially by the synthetic production of oligopeptides which contain sequences of portions of the antigen which can be predicted from the results of immunochemical tests on fragments of the proteins produced in bacteria or generated as a result of chemical or enzymatic cleavage of the native or recombinant peptides.

According to a twelfth embodiment of this invention there is provided an antibody generated against an epitope of the eleventh embodiment. These antibodies or idiotypes can be used for passive protection of animals.

According to a thirteenth embodiment of this invention there is provided an antibody generated against the variable region of an antibody of the twelfth embodiment, a so called anti-idiotype antibody, which mimics a protective epitope of the antigen and may be used as an effective vaccine in active immunization of animals.

According to a fourteenth embodiment of this invention there is provided a vaccine comprising an effective amount of one or more antigens of the first embodiment, expression products of the ninth embodiment, epitopes of the eleventh embodiment and/or anti-idiotype antibodies of the thirteenth embodiment, together with a pharmaceutically acceptable excipient, carrier, adjuvant and/or diluent.

Preferred vaccines include those suitable for injectable or oral administration. Preferably, injectable vaccines include a pharmaceutically acceptable adjuvant.

According to a fifteenth embodiment of this invention there is provided an antibody prepared as a result of vaccination of a host by administration of one or more antigens, expression products, epitopes, anti-idiotype antibodies and/or vaccines of the present invention to the host. Such antibodies include polyclonal and monoclonal antibodies. It is recognised that there are compounds which act in a manner similar to the antibodies of the fifteenth embodiment. Although these compounds are not antibodies their presence in the host can produce a similar protective effect to the antibodies. Throughout the specification and claims, reference to antibodies of the fifteenth embodiment should be construed as extending to these compounds.

According to a sixteenth embodiment of this invention there is provided: an antibody composition comprising at least one antibody of the twelfth and/or fifteenth embodiment together with a pharmaceutically acceptable carrier, diluent and/or excipient.

According to a seventeeth embodiment of this invention, there is provided a process for the preparation of an antigen of the first embodiment which process comprises: collecting excretory-secretory fluids from a parasitic nematode species; fractionating the fluid by lentil lectin chromatography with methylmannoside as eluent; collecting the bound and unbound fractions; further fractionating by SDS-gel electrophoresis; and electroeluting the antigen.

According to an eighteenth embodiment of this invention there is provided a process for the preparation of a fused gene of the fifth embodiment which process comprises providing a promoter, a translation start signal and a DNA sequence of the third embodiment and operatively linking the promoter, translation start signal and DNA sequence.

According to a nineteenth embodiment of this invention there is provided a process for the preparation of a vaccine of the fourteenth embodiment which process comprises admixing an effective amount of at least one antigen of the first embodiment and/or expression product of the ninth embodiment and/or epitope of the eleventh embodiment and/or anti-idiotype antibody of the thirteenth embodiment with a pharmaceutically acceptable carrier, diluent, excipient and/or adjuvant.

According to a twentieth embodiment of this invention there is provided a process for the preparation of an antibody of the fifteenth embodiment which process comprises immunizing an immunoresponsive host with an antigen of the first embodiment and/or expression product of the ninth embodiment and/or epitope of the eleventh embodiment and/or anti-idiotype antibody of the thirteenth embodiment and/or a vaccine of the fourteenth embodiment.

According to a twenty-first embodiment of this invention there is provided a process for the preparation of an antiidiotype antibody of the thirteenth embodiment which process comprises immunizing an immunoresponsive host with an antibody of the twelfth embodiment.

According to a twenty-second embodiment of this invention there is provided a process for the preparation of an antibody composition of the sixteenth embodiment which process comprises: admixing an effective amount of at least one antibody of the twelfth and/or fifteenth embodiment with a pharmaceutically acceptable carrier, diluent and/or excipient.

According to a twenty-third embodiment of this invention there is provided a method of protecting a host in need of such treatment from infection by a parasitic nematode species which method comprises vaccinating the host with an antigen, expression product, vaccine, epitope and/or anti-idiotype antibody of the invention.

According to a twenty-fourth embodiment of this invention there is provided a method of passively protecting a host in need of such treatment against infection by a parasitic nematode species which method comprises passively vaccinating the host with at least one antibody of the twelfth and/or fifteenth embodiment and/or antibody composition of the sixteenth embodiment.

It is recognised that variation in amino acid and nucleotide sequences can occur between different allelic forms of a particular protein and the gene(s) encoding the protein. Further, once the sequence of a particular gene or protein is known, a skilled addressee, using available techniques, would be able to manipulate those sequences in order to alter them from the specific sequences obtained to provide a gene or protein which still functions in the same way as the gene or protein to which it is related. These molecules are referred to herein as "homologues" and are intended also to be encompassed by the present invention.

In this regard, a "homologue" is a polypeptide that retains the basic functional attribute, namely, the protective activity of an antigen of the invention, and that is homologous to an antigen of the invention. For purposes of this description, "homology" between two sequences connotes a likeness short of identity indicative of a derivation of the first sequence from the second. In particular, a polypeptide is "homologous" to an antigen of the invention if a comparison of amino acid sequences between the polypeptide and the antigen, reveals an identity of greater than about 70% over 20 amino acids. Such a sequence comparison can be performed via known algorithms, such as the one described by Lipman and Pearson (1985), which are readily implemented by computer.

Homologues can be produced in accordance with the present invention, by conventional site-directed mutagenesis, which is one avenue for routinely identifying residues of the molecule that can be modified without rendering the resulting polypeptide biologically inactive. oligonucleotide-directed mutagenesis, comprising [i] synthesis of an oligonucleotide with a sequence that contains the desired nucleotide substitution (mutation), [ii] hybridizing the oligonucleotide to a template comprising a structural sequence coding for an antigen of the invention and [iii] using T4 DNA polymerase to extend the oligonucleotide as a primer, is preferred because of its ready utility in determining the effects of particular changes to the antigen sequence.

Also exemplary of antigen homologues within the present invention are molecules that comprise a portion of the antigen without being coincident with the natural molecule, and that display the protective activity of an antigen of the invention.

Also, encompassed by the present invention are synthetic polypeptides that (i) correspond to a portion of the antigen amino-acid sequence and (ii) retain protective activity characteristic of the antigen. Such synthetic polypeptides would preferably be between 6 and 30 amino residues in length.

Whether a synthetic polypeptide meeting criterion (i) also satisfies criterion (ii) can be routinely determined by assaying for protective activity, in an appropriate host.

The amount of antigen, expression product, epitope and/or anti-idiotype antibody that may be combined with carrier, excipient, diluent and/or adjuvant to produce a single vaccine dosage form will vary depending upon the infection being treated or prevented, the host to be treated and the particular mode of administration.

It will be understood, also, that the specific dose level for any particular host will depend upon a variety of factors including the activity of the specific antigen, expression product, epitope, anti-idiotype antibody and/or vaccine employed, the age, body weight, general health, sex, diet, time of administration, route of administration, rate of excretion, drug combination, the particular infection to be treated or prevented and the severity of the particular infection undergoing treatment or prevention.

The vaccine of the present invention may be administered orally or parenterally, in unit dosage formulations containing conventional, non-toxic, pharmaceutically acceptable carriers, diluents, adjuvants and/or excipients as desired.

Injectable preparations, for example, sterile injectable aqueous or oleagenous suspensions may be formulated according to known arts using suitable dispersing or wetting agents and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The term "pharmaceutically acceptable adjuvant" can mean either the standard compositions which are suitable for human administration or the typical adjuvants employed in animal vaccinations. An appropriate adjuvant can be selected using ordinary skill in the art.

Suitable adjuvants for the vaccination of animals and humans include but are not limited to aluminium hydroxide and oil emulsions such as Marcol 52: Montanide 888 (Marcol is a Trademark of Esso. Montanide is a Trademark of SEPPIC, Paris.). Other adjuvants suitable for use in the present invention include conjugates comprising the expression product together with an integral membrane protein of prokaryotic or eukaryotic origin, such as TraT.

Routes of administration, dosages to be administered as well as frequency of injections are all factors which can be optimized using ordinary skill in the art. Typically, the initial vaccination is followed some weeks later by one or more "booster" vaccinations, the net effect of which is the production of vigorous immunological responses such as high titres of antibodies against the antigen epitope, anti-idiotype antibody or expression product.

Solid dosage forms for oral administration may include capsules, tablets, pills, powders, and granules. In such solid dosage forms, antigens, epitopes, anti-idiotype antibodies and/or expression products may be admixed with at least one inert diluent such as sucrose, lactose or starch. Such dosage forms may also comprise, as is normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include nanoparticles, microcapsules, LTB conjugates, cholera or its B subunit as a conjugate, in pharmaceutically acceptable emulsions, syrups, solutions, suspensions, and elixirs containing inert diluents commonly used in the art, such as water. Such compositions may also comprise adjuvants, such as wetting agents, emulsifying and suspending agents or TraT as a conjugate, and sweetening, flavouring, and perfuming agents including sugars such as sucrose, sorbitol, fructose, etc., glycols such as polyethylene glycol, propylene glycol etc, oils such as sesame oil, olive oil, soybean oil etc., antiseptics such as alkylparahydroxybenzoate etc, and flavours such as strawberry flavour, peppermint etc.

BRIEF DESCRIPTION OF THE DRAWINGS

FIG. 1 illustrates the structure of a Tra T—Tc Ad ESA 1 fusion (SEQ ID NOS. 28 and 29).

BEST MODE AND OTHER MODES OF CARRYING OUT THE INVENTION

The nucleotide sequences, fused genes, recombinant DNA molecules and transformed hosts of the invention are prepared using standard techniques of molecular biology such as those described in Maniatis et al (1982).

In preparing the nucleotide sequences of the invention, it is recognised that the genes of interest, and also cDNA copies made from the genes may be provided in low yield. PCR (polymerase chain reaction) techniques can be used to amplify the relevant DNA to facilitate detection and cloning.

Expression products of the invention are obtained by culturing the transformed hosts of the invention under standard conditions as appropriate to the particular host and separating the expression product from the culture by standard techniques. The expression product may be used in impure form or may be purified by standard techniques as appropriate to the expression product being produced and the particular host.

The vaccines of the invention are prepared by mixing, preferably homogeneously mixing, antigen, expression product, anti-idiotype antibody and/or epitope with a pharmaceutically acceptable carrier, diluent, excipient and/or adjuvant using standard methods of pharmaceutical preparation.

The amount of antigen, expression product, anti-idiotype antibody and/or epitope required to produce a single dosage form will vary depending upon the infection to be treated or prevented, the host to be treated and the particular mode of administration. The specific dose level for any particular host will depend upon a variety of factors including the activity of the antigen, expression product, anti-idiotype antibody and/or epitope employed, the age, body weight, general health, sex, and diet of the host, time of administration, route of adminstration, rate of excretion, drug combination and the severity of the infection undergoing treatment.

The vaccine may be administered orally or parenterally in unit dosage formulations containing conventional, non-toxic, pharmaceutically acceptable carriers, diluents, excipients and/or adjuvants as desired.

Antibodies are raised using standard vaccination regimes in appropriate hosts. The host is vaccinated with an antigen, expression product, epitope, anti-idiotype antibody and/or vaccine of the invention.

The compounds acting in a similar manner to the antibodies of the invention may be purified naturally occuring compounds or synthetically prepared using standard techniques including standard chemical or biosynthetic techniques.

The antibody composition is prepared by mixing, preferably homogeneously mixing, antibody with a pharmaceutically acceptable carrier, diluent and/or excipient using standard methods of pharmaceutical preparation.

The amount of antibody required to produce a single dosage form will vary depending upon the infection to be treated or prevented, host to be treated and the particular mode of administration. The specific dose level for any particular host will depend upon a variety of factors including the activity of the antibody employed, the age, body weight, general health, sex and diet of the host, time of administration, route of administration, rate of excretion, drug combination and the severity of the infection undergoing treatment.

The antibody composition may be administered orally or parenterally in unit dosage formulations containing conventional, non-toxic, pharmaceutically acceptable carriers, diluents and/or excipients as desired.

The invention is further described with reference to the following Examples.

EXAMPLE 1

Preparation of Excretory/secretory Antigens (ESA) From Adult *T. colubriformis*.

Young merino Border Leicester cross bred lambs 12 months old and reared worm free were infected with 60,000 infective larvae of *T. colubriformis*. Twenty one days post-infection, the sheep were slaughtered and the nematodes were recovered from the intestine by Baermanization. The worms were washed in RPMI 1640 culture medium containing penicillin (100 units/ml) and streptomycin (100 $\mu$g/ml) and incubated in the same medium (approximately 1000 worms/ml) for 16 h at 37° C. in an incubator with 5% $CO_2$. The viability of the worms was monitored by visual inspection and routinely more than 95% were alive and motile.

The worms and large debris were removed from the culture media by filtration or centrifugation. The supernatant or filtrate thus obtained is referred to as adult ESA (Tc Ad ESA).

Similar preparations referred to as Tc L4 ESA have been made from *T. colubriformis* fourth stage larvae recovered from sheep after 7–8 days infection. The subsequent analysis of the components of the extracts by polyacrylamide gel electrophoresis in the presence of sodium dodecylsulphate (SDS-PAGE) showed that L4 and adult extracts contained similar antigens but the extracts from the adults have been used in preference as they yielded more material than L4 extracts.

EXAMPLE 2

Vaccination of Guinea Pigs With L4 ESA and Adult ESA.

Excretory/secretory antigens were prepared from L4 and adult *T. colubriformis* as described in Example 1. This material was used to vaccinate guinea pigs intraperitoneally using the procedure described by O'Donnell et al (1985). It can be seen (Tables 1 and 2) that the ESA from L4 or young adult nematodes gave highly significant protection in each experiment (62–92% reduction in parasitism).

TABLE 1

Protection of Guinea Pigs with L4 ESA and Fractions derived from it by Lentil Lectin Affinity Chromatography

| Expt No. | Group | Antigen | Injected ($\mu$g) | n | Worm Numbers (mean ± SD) | Protection (%) |
|---|---|---|---|---|---|---|
| 110 | Controls | | | 7 | 556 ± 152 | |
| | Vaccinates | L4 ESA | 60 | 5 | 94 ± 122 | 83 |
| 112 | Controls | | | 5 | 655 ± 463 | |
| | Vaccinates | L4 ESA | 100 | 5 | 249 ± 547 | 62 |
| 121 | Controls | | | 10 | 1103 ± 336 | |
| | Vaccinates | L4ESA (collected 0–24 h) | 100 | 5 | 82 ± 127 | 93 |
| | Vaccinates | L4ESA (collected 48–72 h) | 100 | 8 | 190 ± 159 | 83 |
| 120 | Controls | | | 6 | 821 ± 442 | |
| | Vaccinates | Total ESA(L4) | 50 | 5 | 103 ± 144 | 87 |
| | Vaccinates | LL$^+$ (L4) | 12 | 4 | 193 ± 141 | 76 |
| | | LL$^-$ (L4) | 50 | 5 | 51 ± 51 | 94 |
| 123 | Controls | | | 7 | 1103 ± 314 | |
| | Vaccinates | Total ESA (L4) | 54 | 5 | 83 ± 57 | 92 |
| | Vaccinates | LL$^+$ (L4) | 22 | 4 | 158 ± 142 | 86 |
| | Vaccinates | LL$^-$ (L4) | 200 | 5 | 191 ± 149 | 83 |

Vaccinates were injected intraperitoneally with the relevant antigen (n indicates the number of guinea pigs in each group). Animals were challenged with 2000 larvae 28 days later and killed for worm counts 13 days post challenge. LL$^+$ is material bound and eluted from the lentil lectin column. LL$^-$ is the unbound, run through material.

TABLE 2

Protection of Guinea Pigs with Adult ESA and Fraction Derived from it by Lentil Lectin Affinity Chromatography

| Expt No. | Group | Antigen | Injected ($\mu$g) | n | Worm Numbers | Protection (%) |
|---|---|---|---|---|---|---|
| 126 | Controls | | | 8 | 1069 ± 343 | |
| | Vaccinates | Ad ESA | 100 | 8 | 300 ± 239 | 72 |

TABLE 2-continued

Protection of Guinea Pigs with Adult ESA and Fraction
Derived from it by Lentil Lectin Affinity Chromatography

| Expt No. | Group | Antigen | Injected (μg) | n | Worm Numbers | Protection (%) |
|---|---|---|---|---|---|---|
| 164 | Controls | | | 5 | 910 ± 243 | |
| | Vaccinates | Ad ESA | 50 | 5 | 140 ± 211 | 85 |
| | Vaccinates | Ad ESA LL$^+$ | 25 | 4 | 219 ± 277 | 76 |
| | Vaccinates | Ad ESA LL$^+$ | 50 | 4 | 544 ± 348 | 40 |
| 280 | Controls | | | 11 | 1484 ± 375 | |
| | Vaccinates | Ad ESA | 10 | 9 | 254 ± 435 | 83 |

Vaccinates were injected intraperitoneally with the relevant antigen (n indicates the number of guinea pigs in each group). Animals were challenged with 2000 larvae 28 days later and killed for worm counts 13 days post challenge. LL$^+$ is material bound and eluted from the lentil lectin column. LL$^-$ is the unbound, run through material.

EXAMPLE 3
Fractionation of Adult ESA

The culture supernatant was concentrated 40 fold on a "Diaflo" (Amicon) YM10 membrane. The concentrated fluid was absorbed onto a lentil lectin Sepharose-4B (Pharmacia) column (5×1 cm) equilibrated with Tris-buffered saline (TBS; 10 mM Tris, 150 mM NaCl, pH 7.4). The column was washed with 100 ml of TBS at a flow rate of 1 ml/min and fractions containing unabsorbed material (measured by absorbance at 280 nm) were collected. The specifically bound glycopeptides were eluted from the column using a solution of 2% methylmannoside in TBS. Fractions containing material absorbing at 280 nm were pooled. Both the lentil lectin bound (LL$^+$) and unbound (LL$^-$) components were precipitated from solution by the addition of 10 volumes of methanol, chilling the mixture at −20° C. for 16 hours and centrifugation at 12,000×g for 15 min.

When analysed by SDS-PAGE (FIG. 1) the LL$^+$ fraction contained Coomassie staining bands with apparent molecular weights 81, 37, 32 and 30 kilodaltons (kD) together with some smaller molecular weight material when compared with molecular weight standards. The LL$^-$ fraction contained several components including predominant bands at about 28–32, 17 and 10–12 kilodaltons.

EXAMPLE 4
Vaccination of Guinea Pigs with Lentil Lectin Fractionated L4 and Adult ESA.

The material prepared from L4 or adult ESA by lentil lectin chromatography was used to vaccinate guinea pigs intraperitoneally (O'Donnell et al 1985). Both the bound material and the unbound fraction gave highly significant degrees of protection to subsequent challenge of those guinea pigs with *T. colubriformis* (Tables 1 and 2). It is thus clear that there are components in both the bound and flow through fractions which are capable of eliciting a protective immune response following vaccination.

EXAMPLE 5
Further Fractionation of Lentil Lectin Bound and Unbound Components of Adult ESA and Recovery of Individual Antigens from Preparative SDS Gels.

Samples of the LL$^+$ and LL$^-$ fractions from adult ESA (100–500 mg protein) were suspended in Laemmli buffer (Laemmli, 1970) and subjected to electrophoretic separation on preparative 12.5% SDS-polyacrylamide gels. Proteins were visualised with Coomassie R-250 and electroeluted (Stearne et al, 1985).

The components described here that were recovered from the LL$^+$ fraction were Tc Ad ESA1 (SEQ ID NO: 12), with an apparent molecular weight of 30 kD; Tc Ad ESA2 (SEQ ID NO: 6) with an apparent molecular weight of 37 kD and Tc Ad ESA5 with an apparent molecular weight of 81 kD. The components described here that were recovered from the LL$^-$ fraction were Tc Ad ESA3 (SEQ ID NO: 4) with an apparent molecular weight of 17 kD and Tc Ad ESA4 (SEQ ID NO: 25) with an apparent molecular weight of 11 kD.

The LL$^+$ 32 kD component and the LL$^-$ 28–30kD components are believed to be related to the LL$^+$ 30 kD antigen (Tc Ad ESA1), as western transfers resolved with antibodies raised against the purified Tc Ad ESA1 show cross-reaction with these components. These differences are likely to be due at least in part to differential degrees of glycosylation of the Tc Ad ESA1 as analysis of the cloned DNA sequence predicts that this component is extensively glycosylated.

EXAMPLE 6
Vaccination of Guinea Pigs with Purified Antigens

The individual antigens electroeluted from SDS gels were used to vaccinate guinea pigs as described in Example 2. The guinea pigs were challenged with *T. colubriformis* and shown to be significantly protected from parasitism (Tables 3 and 4).

TABLE 3

Protection of Guinea Pigs by Vaccination with Purified
Antigens, Tc Ad ESA1, Tc Ad ESA2 and Tc Ad ESA5, from the
lentil lectin bound fraction (LL$^+$)

| Group | Antigen | Injected (μg) | n | Worm Numbers | Protection (%) |
|---|---|---|---|---|---|
| Experiment 200 | | | | | |
| Controls | | | 12 | 1135 ± 263 | |
| Vaccinates 1 | Total LL$^+$ | 60 | 5 | 354 ± 341 | 69 |
| Vaccinates 2 | Tc Ad ESA1 | 21 | 5 | 458 ± 534 | 60 |
| Vaccinates 3 | Tc Ad ESA2 | 24 | 5 | 482 ± 683 | 57 |
| Vaccinates 4 | Tc Ad ESA5 | 8.5 | 5 | 530 ± 361 | 53 |
| Experiment 218 | | | | | |
| Controls | | | 8 | 1389 ± 773 | |
| Vaccinates | Total LL$^+$ | 10 | 3 | 149 ± 226 | 89 |
| Vaccinates | Tc Ad ESA1 | 20 | 4 | 563 ± 828 | 59 |
| Vaccinates | Tc Ad ESA2 | 10 | 3 | 999 ± 339 | 28 |
| Vaccinates | Tc Ad ESA5 | 10 | 3 | 706 ± 283 | 49 |
| Experiment 257 | | | | | |
| Controls | | | 10 | 482 ± 200 | |
| Vaccinates | Tc Ad ESA1 (deglycosylated) | 12.5 | 5 | 254 ± 170 | 47 |
| Experiment 236 | | | | | |
| Controls | | | 11 | 1223 ± 236 | |
| Vaccinates | Tc Ad ESA1 (deglycosylated) | 17 | 5 | 121 ± 126 | 90 |
| Experiment 267 | | | | | |
| Controls | | | 7 | 652 ± 281 | |
| Vaccinates | Tc Ad ESA1 (in Alhydrogel) | 10 | 5 | 238 ± 178 | 63 |

Vaccinates were injected intraperitoneally with the relevant antigen. Animals were challenged with 2000 larvae 28 days later and killed for worm counts 13 days post challenge (n indicates the number of animals in each group).

TABLE 4

Protection of Guinea Pigs by Vaccination with Purified Antigens Tc Ad ESA3 and Tc Ad ESA4 from the lentil lectin unbound fraction (LL⁻).

| Group | Antigen | Injected (μg) | n | Worm Numbers | Protection (%) |
|---|---|---|---|---|---|
| Experiment 126 | | | | | |
| Controls | | | 5 | 1103 ± 186 | |
| Vaccinates 1 | Tc Ad ESA3 | 40 | 5 | 182 ± 230 | 83 |
| Vaccinates 2 | Tc Ad ESA4 | 20 | 5 | 266 ± 248 | 76 |
| Experiment 241 | | | | | |
| Controls | | | 10 | 773 ± 609 | |
| Vaccinates 1 | Tc Ad ESA3 | 20 | 5 | 310 ± 418 | 60 |
| Vaccinates 2 | Tc Ad ESA4 | 20 | 5 | 338 ± 487 | 56 |

Vaccinates were injected intraperitoneally with antigens isolated from the adult *T. colubriformis* ESA preparations. Animals were challenged with 2000 infective larvae 28 days later and killed for worm counts 13 days post challenge.

It is clear from the results in Tables 3 and 4 that antigens electroeluted from SDS-PAGE of both the LL⁺ and LL⁻ fractions were capable of conferring substantial protection to guinea pigs against challenge infection by *T. colubriformis*. Of particular relevance in this work are the Tc Ad ESA1 (SEQ ID NO: 12), Tc Ad ESA2 (SEQ ID NO: 6) and Tc Ad ESA5 components of the LL⁺ fraction and the Tc Ad ESA3 (SEQ ID NO: 4) and Tc Ad ESA4 (SEQ ID NO: 25) components of the LL⁻ fraction. Other Tc Ad ESA components also had effects and are of relevance.

Vaccination of guinea pigs with Tc Ad ESA1 adjuvanted in Alhydrogel resulted in 63% protection being obtained. Deglycosylation of Tc Ad ESA1 did not result in a decrease in the extent of protection obtained (in experiment 257, the worm numbers in the controls were abnormally low) indicating that the protein portion of the molecule was capable of giving protection: the carbohydrate was apparently not the protective component.

EXAMPLE 7

Amino Acid Sequence Analysis of Isolated Peptides

The polypeptides isolated as described in Example 5 were analysed for N-terminal amino acid sequence on an Applied Biosystems gas phase amino acid sequencer. To obtain internal sequences, purified protein was digested with proteinase [37° C., overnight, in 0.1M NH₄HCO₃ pH 7.8 at 5% w/w enzyme/substrate ratio]. Peptides were separated by HPLC using a 30×2.1 mm Aquapore RP-300 column with a gradient of 0.1% TFA to 0.1% TFA/70% acetonitrile. Some of the amino acid sequences obtained are shown in Table 5: the underlined sequences were found to be particularly useful in providing information to design oligonucleotide probes suitable for isolation of CDNA clones.

TABLE 5

Some N-terminal and Internal Amino Acid Sequences from Tc Ad ESA1-5

| | | |
|---|---|---|
| Tc Ad ESA1 | | (SEQ ID NO:12) |
| Amino Terminal sequence: | A N N K X Q X <u>D I E O L M P K Y</u> | (SEQ ID NO:31) |
| Armillaria proteinase peptides: | K E Y S | (SEQ ID NO:1) |
| | K L I X D | (SEQ ID NO:2) |
| Tc Ad ESA2 | | (SEQ ID NO:6) |
| Armillaria proteinase peptides: | S S L | |
| | K V I P X <u>N P P I K D T P</u> | (SEQ ID NO:7) |
| Tc Ad ESA3 | | (SEQ ID NO:4) |
| Amino Terminal sequence: | K S <u>D E E I I K D A L</u> S A L | (SEQ ID NO:8) |
| Armillaria proteinase peptide: (overlap with N-terminal sequence) | K D A L S A L D V V P L G S | (SEQ ID NO:15) |
| Tc Ad ESA4 | | (SEQ ID NO:25) |
| Tryptic peptides: | R L A D D S D F G | (SEQ ID NO:20) |
| | N Y D <u>W M K G O W O</u> N | (SEQ ID NO:21) |
| Tc Ad ESA5 | | |
| Amino Terminal sequence: | S X S L K D | (SEQ ID NO:26) |

For Tc Ad ESA1 (SEQ ID NO: 12), amino acid analysis after reduction and carboxymethylation (O'Donnell et al., 1973) indicated the presence of 2 residues of half-cystine. Deglycosylation of Tc Ad ESA1 with N-glycanase (Genzyme), which removes asparagine-linked carbohydrate, reduced the apparent molecular weight from 30 kD to 15 kD. This is in close accordance with information provided by the cDNA sequence (see below).

Deglycosylation of Tc Ad ESA2 (SEQ ID NO: 6) by the same treatment reduced the apparent molecular weight as analysed by SDS-PAGE from 37 kD to approximately 30 kD. A tryptic peptide from digestion of deglycosylated Tc Ad ESA 2 gave the sequence E-I-A-D-D/S-S-K-R (SEQ ID NO: 13, wherein Xaa is Asp or Ser).

EXAMPLE 8
Isolation of Recombinant Organisms Containing the Genes Coding for the Tc Ad ESA Components A. Construction of cDNA Libraries.

Messenger RNA was isolated from the L4 stage of *T. colubriformis* by grinding the larvae in a buffer containing guanidine hydrochloride (6M) sodium acetate (0.2M pH 5.2), and 2-mercaptoethanol (50 mM), precipitation with ethanol and fractionation on an oligo(dT)-cellulose column. The L4 PolyA$^+$ mRNA was used as the template for synthesis of double-stranded cDNA using the Amersham ribonuclease H/DNA polymerase I kit (Amersham cDNA synthesis system, #RPN.1256) as recommended by the manufacturers. Following the addition of EcoRI linkers, the double-stranded cDNA was ligated to lambda gt11 and packaged into viable bacteriophage which were used to infect *E. coli* Y1090 cells, essentially as described by Huynh et al (1985). Using the above methods, a cDNA library was established consisting of $2\times10^5$ independent recombinants. A similar technique was used to establish an adult cDNA library in lambda gt 10 containing $1.5\times10^5$ independent recombinants.

B. Oligonucleotide probes i) Tc Ad ESA1 (SEQ ID NO: 12)

The amino acid sequence (SEQ ID NO: 9) D I E Q L M P was used to design a degenerate oligonucleotide probe (SEQ ID NO: 10)

```
5' G G C A T A A G T T G T T C A A T A T C 3'
             G     C     C     G     G
             C
``` ii) Tc Ad ESA2 (SEQ ID NO: 6)

The amino acid sequence N P P I K D T P was used to design a degenerate oligonucleotide probe using deoxyinosine in positions of 4-fold degeneracy (SEQ ID NO: 32)

```
          A     T                             A
5' G G L G T G T C C T T I A T I G G I G G G T T 3'
``` iii) Tc Ad ESA3 (SEQ ID NO: 4)

The amino acid sequence (SEQ ID NO: 16) D E E I I K D A was used to design a degenerate oligonucleotide probe (SEQ ID NO: 17)

```
    A     T                 T     T     A
5' G C G T C C T T T A T T A T C T C C T C G T C
``` iv) Tc Ad ESA4 (SEQ ID NO: 25)

The amino acid sequence (SEQ ID NO: 22) W M K G Q W Q N was used to design an oligonucleotide probe (SEQ ID NO: 23)

```
5' T T T T G C C A T T G I C C T T T C A T C C A 3'
``` v) Tc Ad ESA5

```
                                   (SEQ ID NO:27)
   G     T           G
5' A T C C T T I A A I G A I I I I G A 3'
```

All oligonucleotides are the reverse complement of the DNA sequence coding for the amino acid sequences selected.

C. Selection of Recombinants from cDNA Libraries

The L4 and young adult cDNA libraries in lambda gt11 and gt10 respectively were amplified and aliquots were screened using the above synthetic oligonucleotides to probe duplicate filter lifts as described by Wallace et. al. [1985] and Benton and Davis [1977].

D. Sequence of cDNA Clones

A number of the selected clones contained an insert which could be resected with EcoRI and subcloned into M13mp18 digested with the same enzyme. The DNA sequences of the subcloned inserts were determined using the method of Sanger et. al. [1980]The DNA sequence of several clones of the Tc Ad ESA1 CDNA was determined and is summarised in Table 6. The DNA sequence contains an open reading frame which codes for a protein of 130 amino acids. The N-terminal amino acid sequence corresponds to the sequence obtained by gas phase sequence analysis of the antigen isolated from Ad ESA1 (underlined in Table 6, also shown in SEQ ID NO: 11,) and the two internal peptide sequences obtained from *Armillaria mellea* digests of Tc Ad ESA1 can also be identified (SEQ ID NOs. 31 , 1, and 2 respectively). An *E. coli* strain, TG1, transformed with plasmid vector pTTQ18 containing the Tc Ad ESA 1 gene (SEQ ID NO: 11) has been given the inhouse reference number BTA 1689, and has been deposited at the American Type Culture Collection 10801 University Boulevard, Manassas, Va. 20110-2209 under accession number ATCC 68099. Sequence of the DNA from several isolates has shown some variation in the translated amino acid sequence. The amino acids which have varied are doubly underlined in Table 6. The sequence corresponding to the mature protein has been determined. The sequence of the presumed N-terminal leader sequence has yet to be established. The amino acid sequence shows four sites of potential N-linked glycosylation (consensus sequence AsnXSer/Thr) which is consistent with the lentil lectin binding properties of this antigen and with the altered mobility of the antigen in SDS-PAGE following treatment with N-glycanase. Finally, the molecular weight calculated from the amino acid sequence shown (15,300 daltons) is in close agreement with that obtained for the N-glycanase treated antigen.

TABLE 6

DNA sequence (SEQ ID NO:11) of the cDNA coding for Tc Ad ESA1 and the translated amino acid sequence (SEQ ID NO:12) coding for the complete mature protein.

```
                10          20          30              40
                 *           *           *               *
GAA TTC GGG GGC AAC ACT TAC AGT GCA AAC AAT AAG CAA CAG ACC
                                Ala Asn Asn Lys Gln Gln Thr 50          60            70          80            90
       *           *             *           *             *
GAC ATA GAA CAA CTC ATG CCC AAA TAT AAC TCG ACG TTC GCG AAG
```

TABLE 6-continued

DNA sequence (SEQ ID NO:11) of the cDNA coding for Tc Ad ESA1 and the translated amino acid sequence (SEQ ID NO:12) coding for the complete mature protein.

```
Asp Ile Glu Gln Leu Met Pro Lys Tyr Asn Ser Thr Phe Ala Lys 100           110           120           130
           *             *             *             *
ATG AAT GGA AAC TAT AGT TAT AAG CTG ATC TGG GAT GAC AGC ATG
Met Asn Gly Asn Tyr Ser Tyr Lys Leu Ile Trp Asp Asp Ser Met 140           150           160           170           180
       *             *             *             *             *
GTA TCT GAT GCG CTG CAA GAA GCA AAG GAG CAA TAC AGT ACG AAT
Val Ser Asp Ala Leu Gln Glu Ala Lys Glu Gln Tyr Ser Thr Asn 190           200           210           220
           *             *             *             *
GCT ACC TTC AAG ATC CGT CGG AGA AAG GTG TTC ATA AAG GGC GAT
Ala Thr Phe Lys Ile Arg Arg Arg Lys Val Phe Ile Lys Gly Asp 230           240           250           260           270
       *             *             *             *             *
AAC GCA ACG ATG GAG GAA AAA GTG GAG GGA GCT CTG AAG TAC CCC
Asn Ala Thr Met Glu Glu Lys Val Glu Gly Ala Leu Lys Tyr Pro 280           290           300           310
           *             *             *             *
GTC TTG AGA GCC GAT AAA TTT CTT CGC CGT CTT CTC TGG TTC ACA
Val Leu Arg Ala Lys Phe Leu Arg Arg Leu Leu Trp Phe Thr 320           330           340           350           360
       *             *             *             *             *
CAC TAC GCA TGC AAT GGA TAT TAC GAT ACG AAA GGT GGA CAC GAT
His Tyr Ala Cys Asn Gly Tyr Tyr Asp Thr Lys Gly Gly His Asp 370           380           390           400
           *             *             *             *
GTC CTG ACT GTC GCG TGT CTC TAC AGA GAG ATC GAT TAC AAA AAT
Val Leu Thr Val Ala Cys Leu Tyr Arg Glu Ile Asp Tyr Lys Asn 410           420           430           440           450
       *             *             *             *             *
TCT CAC TAT TAG AAA GCA GTC AAC AAA AAC AGC AGA GTA AAC TGA
Ser His Tyr ---

460           470           480           490
           *             *             *             *
CTG CAC ATT TCC GCA GTT TTT GAA TAA ATA CTT GAT GCA ACT CAA
          500
           *
AAA AAA AAA AAA
```

The DNA sequence of the clone coding for Tc Ad ESA4 (SEQ ID NO: 25) is shown in Table 7. The DNA sequence contains an open reading frame which codes for a protein of 95 amino acids, and contains only a single potential glycosylation site. *E coli* strain TG1 transformed with an inhouse pBR322 based vector, pBTA503, containing the Tc Ad ESA4 gene (SEQ ID NO: 24) has been given the inhouse reference number BTA 1690 and has been deposited at the American Type Culture Collection 10801 University Boulevard, Manassas, Va. 20110-2209 under accession number ATCC 68100. The lack of binding to the lentil lectin column and the close agreement between the estimated molecular weight on SDS-PAGE and the predicted molecular weight based on the sequence suggests the protein is not glycosylated.

TABLE 7

DNA sequence (SEQ ID NO:24) of the cDNA coding for Tc Ad ESA4 and the translated amino acid sequence (SEQ ID NO:25)

```
TACAAGACCC CCAATTGTAC ACGAAATTCT TCAACGAAGA AAACAGCCTA AATCTGAGAT

GGAACCCACA T ATG TCG CAG CAT GCT CTA CAA GAA ATT GAG AAG CCA GGG
             Met Ser Gln His Ala Leu Gln Glu Ile Glu Lys Pro Gly
             1               5                   10
```

TABLE 7-continued

DNA sequence (SEQ ID NO:24) of the cDNA coding for Tc Ad ESA4 and the translated amino acid sequence (SEQ ID NO:25)

```
AAA TTT TCG CAA AAA GAT TCA GCA TAT TTC AAG CTC GAA AAC AAG AGG
Lys Phe Ser Gln Lys Asp Ser Ala Tyr Phe Lys Leu Glu Asn Lys Arg
     15              20              25

GAA CTG AAG GGA GAC AAT CTA CCA GTG GAG GAG AAA GTA CGC CAA ACT
Glu Leu Lys Gly Asp Asn Leu Pro Val Glu Glu Lys Val Arg Gln Thr
 30              35              40                          45

ATT GAA AAA TTC AAG GAT GAT GTA AGC GAA ATC AGA CGT CTC GCT GAT
Ile Glu Lys Phe Lys Asp Asp Val Ser Glu Ile Arg Arg Leu Ala Asp
             50              55                      60

GAT TCG GAT TTT GGA TGC AAC GGC AAA GAA ACC GAG GGT GCA ATG CAC
Asp Ser Asp Phe Gly Cys Asn Gly Lys Glu Thr Glu Gly Ala Met His
                 65              70              75

ATT GTG TGT TTC TTC CAG AAG AAT TAT GAC TGG ATG AAA GGA CAA TGG
Ile Val Cys Phe Phe Gln Lys Asn Tyr Asp Trp Met Lys Gly Gln Trp
             80              85              90

CAA AAC TGATTTTTCT GAAGTACTTG TTGGATTCTT CGTAGAATCG ATGCACAAAA
Gln Asn
     95

TACCTTTTTT GGGAGACAAC TTCGCATAAA ACTTCTCGAT GAAAAAAAAA AAAAA
```

The DNA sequence of the partial clone coding for Tc Ad ESA3 is shown in Table 8 and in SEQ ID NO: 18. The DNA contains an open reading frame which codes for a peptide of 43 amino acids. The sequence corresponding to the N-terminal amino acid sequence from the natural protein is underlined. An *E. coli* strain DH5αF (BRL) transformed with plasmid pT$_7$T$_3$ (Pharmacia) containing the Tc Ad ESA3 gene fragment shown in Table 8 has been given the inhouse reference number BTA 1691, and has been deposited at the American Type Culture Collection 10801 University Boulevard, Manassas, Va. 20110-2209 under accession number ATCC 68098.

In addition, the full length sequence of the TcAdESA3 coding region has now been shown to be as indicated in Table 9 and in SEQ ID NO: 3.

TABLE 8

DNA sequence (SEQ ID NO:18) of partial cDNA coding for Tc Ad ESA3 and the translated amino acid sequence (SEQ ID NO:19)

```
                10              20              30              40
                 *               *               *               *
        CGG TTC CTT CTT CTA GCA GCG TTC GTC GCC TAT GCG TAT GCA AAG
        Arg Phe Leu Leu Leu Ala Ala Phe Val Ala Tyr Ala Tyr Ala Lys 50              60              70              80              90
             *               *               *               *               *
        TCA GAT GAA GAA ATC CGA AAA GAT GCA CTA TCT GCT CTG GAT GTA
        Ser Asp Glu Glu Ile Arg Lys Asp Ala Leu Ser Ala Leu Asp Val 100             110             120
                     *               *               *
        GTT CCA CTG GGT TCG ACT CCC GAA AAA CTG GAA AAT GGC
        Val Pro Leu Gly Ser Thr Pro Glu Lys Leu Glu Asn Gly
```

TABLE 9

DNA sequence (SEQ ID NO:3) of cDNA coding for Tc Ad ESA3 and the translated amino acid sequence (SEQ ID NO:19)

```
ATG CGG TTC CTT CTT CTA GCA GCG TTC GTC GCC TAT GCG TAT GCA AAG
Met Arg Phe Leu Leu Leu Ala Ala Phe Val Ala Tyr Ala Tyr Ala Lys
 1               5              10              15

TCA GAT GAA GAA ATC CGA AAA GAT GCA CTA TCT GCT CTG GAT GTA GTT
Ser Asp Glu Glu Ile Arg Lys Asp Ala Leu Ser Ala Leu Asp Val Val
             20              25              30
```

TABLE 9-continued

DNA sequence (SEQ ID NO:3) of cDNA coding for Tc Ad ESA3
and the translated amino acid sequence (SEQ ID NO:19)

```
CCA CTG GGT TCG ACT CCC GAA AAA CTG GAA AAT GGC AGG GAA TTC TAC
Pro Leu Gly Ser Thr Pro Glu Lys Leu Glu Asn Gly Arg Glu Phe Tyr
            35                  40                  45

AAA TAC TTC TTC ACC AAC CAT CAA GAT TTG CGC AAA TAC TTC AAG GGT
Lys Tyr Phe Phe Thr Asn His Gln Asp Leu Arg Lys Tyr Phe Lys Gly
 50                  55                  60

GCC GAA ACT TTC ACT GCC GAT GAT ATC GCT AAG AGC GAC AGA TTC AAG
Ala Glu Thr Phe Thr Ala Asp Asp Ile Ala Lys Ser Asp Arg Phe Lys
 65                  70                  75                  80

AAA CTG GGC AAT CAG CTG CTT CTG TCA GTG CAT CTT GCC GCT GAC ACC
Lys Leu Gly Asn Gln Leu Leu Leu Ser Val His Leu Ala Ala Asp Thr
                 85                  90                  95

TAC GAC AAC GAG ATG ATC TTC CGT GCA TTC GTC CGT GAT ACC ATC GAC
Tyr Asp Asn Glu Met Ile Phe Arg Ala Phe Val Arg Asp Thr Ile Asp
                100                 105                 110

CGA CAT GTC GAT CGT GGA CTT GAC CCC AAG CTG TGG AAG GAA TTC TGG
Arg His Val Asp Arg Gly Leu Asp Pro Lys Leu Trp Lys Glu Phe Trp
            115                 120                 125

AGC ATC TAC CAG AAA TTC TTG GAG AGC AAG GGA AAG ACA CTG AGC GCT
Ser Ile Tyr Gln Lys Phe Leu Glu Ser Lys Gly Lys Thr Leu Ser Ala
130                 135                 140

GAT CAG AAG GCT GCA TTT GAC GCC ATT GGC ACG CGA TTC AAC GAT GAG
Asp Gln Lys Ala Ala Phe Asp Ala Ile Gly Thr Arg Phe Asn Asp Glu
145                 150                 155                 160

GCT CAG AAA CAG CTT GCT CAC CAT GGA CTG CCA CAC ACA TAAGAAGTTT
Ala Gln Lys Gln Leu Ala His His Gly Leu Pro His Thr
                165                 170

GCTGAAAACT GTGCGAAGCT TTGTGCATCT TTTTGCTCAA ATAAAGGTCG TTTAGGTAAA

AAAAA
```

The inosine-containing oligonucleotide (SEQ ID NO: 30):

```
5' GG IGT ATC TTT IAT IGG IGG ATT 3'
      G   C             G
``` was used to screen the young adult lambda gt10 cDNA library. The cDNA library was screened with the radiolabeled oligonucleotide as described previously [Sambrook et al., 1989; Wallace et al., 1980] and positively hybridizing plaques were purified through several rounds of screening. Filters were hybridized at 37° C. and washed to a stringency of 6×SSC-0.1% SDS (1×SSC is 15 mM sodium citrate, 150 mM NaCl, pH 7.0), at 40° C. DNA from recombinant lambda clones was prepared using DE52 and CTAB [Manfioletti and Schneider, 1988].

Polymerase Chain Reaction. Uncut, recombinant lambda DNA was subjected to the polymerase chain reaction (PCR) using 25 pmol of lambda gt10 forward and reverse primers (based on the sequences surrounding the EcoRI site) in the presence of 100 μM dNTP's, 16.6 mM ammonium sulphate, 67 mM Tris-HCl pH 8.8, 6.7 mM magnesium chloride and 2.5 units of Taq polymerase (Biotech International). The reaction conditions used were 20 cycles of 95° C. for 1 min, 55° C. for 1 min and 72° C. for 2 min. Following PCR, amplified DNA was phenol:chloroform extracted, ethanol precipitated and then digested with EcoRI. The insert DNA was purified by electroelution from 0.5% agarose andn precipitated in the presence of glycogen.

Cloning into DT7T3/18U and DNA sequencing. EcoRI-digested lambda DNA and PCR-amplified lambda insert DNA were subcloned into the plasmid vector pT7T3/18U (Pharmacia). The subclones were transformed [King and Blakesley, 1986] into Escherichia coli TG1 cells. Single-stranded DNA was prepared using the method supplied with pT7T3/18U (Pharmacia) using M13KO7 helper phage. DNA sequencing was performed with Taq polymerase according to the manufacturer's instructions (Promega) using the universal M13 primer or synthetic oligonucleotides based on previously determined DNA sequences.

Database search. The following databases were searched for protein sequences with homology to Tc Ad ESA2 (SEQ ID NO: 6): EMBL Nucleic Acid Sequence Data Bank, Release 28.0, September 1991; Ooi-Nakashima Protein Sequence Data Bank, March 1986; Protein Identification Resource (PIR), Release 29.0, June 1991; National Biomedical Research Foundation, (NBRF), Release 36.0, March 1991; PRF Protein Sequence Database, Release 91/09 (Peptide Institute, Protein Research Foundation, Osaka, Japan); Genetic Sequence Data Bank (Genbank Release 69.0, September 1991); GBTrans Protein Data Base, Release 13.0, October 1991 (Compiled from Genbank Release 68.0 by The Walter and Eliza Hall Institute of Medical Research, Parkville, Australia); Swiss-Prot Protein Sequence Databank, Release, 19.0, August 1991 (European Molecular Biology Laboratory, FRG); and DNA Data Bank of Japan, Release 8, January 1991. These databases were searched with the whole Tc Ad ESA2 (SEQ ID NO: 6) protein sequence or the sequence lacking the proline rich region (residues 133–169 deleted), using the FASTA program (Pearson/Lipman algorithm) [Pearson & Lipman, 1988].

From 250,000 recombinants screened, four positive clones were purified through rounds of screening and were found to contain inserts of approximately 700–800 bp in size.

Complete DNA sequence data was obtained from the recombinants isolated from the lambda library.

The DNA sequence for the gene is shown in the attached Table (Table 10). The DNA sequence has an uninterrupted reading frame which extends for 701 nucleotides followed by 63 bases of non-coding sequence which contains a polyadenylation addition sequence (AATAAA) but no poly A tail. The predicted amino acid sequence codes for a protein of 220 amino acids, with a molecular weight of 26.4 kilodaltons. The initiating methionine is followed by an eleven amino acid sequence of hydrophobic amino acids which are likely to be a leader sequence which is post-translationally cleaved from the molecule.

The peptide sequence from which the oligonucleotide probe was designed can be seen starting at amino acid 161. The only difference between the peptide sequence and that predicted from the DNA sequence is that Ile 173 is a Thr in the cloned sequence. This is likely to be either a sequencing artefact or represent the variation in the amino acid sequences of various genes within the outbred population (homologues). The predicted amino acid sequence also contains the two other peptide sequences which were obtained from the native polypeptide with some small variation. It can be assured that the cDNA sequence codes for Tc Ad ESA2 (SEQ ID NO: 6). Database searches have not shown any significant homology between the DNA sequence for Tc Ad ESA2 (SEQ ID NO: 6) and genes coding for any other protein.

TABLE 10

DNA sequence (SEQ ID NO:5) of cDNA coding for Tc Ad ESA2
and the translated amino acid sequence (SEQ ID NO:6)

CCTGGTTGTT CCGCACTTTC ACTCGGCGCA GCTCTTCGAC GATG ATG CTG ATC CTT
                                                Met Leu Ile Leu
                                                 1

CTG GCC ATT TTG GTC GGC ACC GTG CCT TCC GAG TCG TCG CTC GTA AAC
Leu Ala Ile Leu Val Gly Thr Val Pro Ser Glu Ser Ser Leu Val Asn
 5                   10                  15                  20

AGT GAC TAT AGG GTT CAC AAT GAC CAC TGT AAA TAC AGT GAG GTT AAG
Ser Asp Tyr Arg Val His Asn Asp His Cys Lys Tyr Ser Glu Val Lys
                 25                  30                  35

CAG CAA CCG TTT AAA GAA ATC GCC AAC TCG TCA CTA CGA TCA TTC CTT
Gln Gln Pro Phe Lys Glu Ile Ala Asn Ser Ser Leu Arg Ser Phe Leu
             40                  45                  50

TTG AGA AAA CTG AGA GGG ATT GGG GAT ACT GAC TGC GTG CAG TCT TAC
Leu Arg Lys Leu Arg Gly Ile Gly Asp Thr Asp Cys Val Gln Ser Tyr
         55                  60                  65

CAA GTG GAG TTC AAC AAC GAC AGC AAT CCG TTT TAT GTC TTT CGC ATC
Gln Val Glu Phe Asn Asn Asp Ser Asn Pro Phe Tyr Val Phe Arg Ile
     70                  75                  80

GAC CGT GAG ACA AGA TTT TCA CGG AAC TAT ACC GTC TGC GGT GTG GTT
Asp Arg Glu Thr Arg Phe Ser Arg Asn Tyr Thr Val Cys Gly Val Val
 85                  90                  95                 100

ACT GTG GTT GGT GGC GAC TTC ATG TGG AAG TCA TGT GAT AAA TCG AAA
Thr Val Val Gly Gly Asp Phe Met Trp Lys Ser Cys Asp Lys Ser Lys
                105                 110                 115

TTC AAA GAC TAT CTT CTA AAG TGT GAG AGC GAA GAG AAC AGA CAT CCA
Phe Lys Asp Tyr Leu Leu Lys Cys Glu Ser Glu Glu Asn Arg His Pro
            120                 125                 130

CAA CTG CCA CCT GTT CTG TCA TGC GAC CGG ACC CCT AAT CCT GTC TCG
Gln Leu Pro Pro Val Leu Ser Cys Asp Arg Thr Pro Asn Pro Val Ser
        135                 140                 145

CCG GTC AGT CCT CCG AAT GAG GAC GCT CCG CCC ACC CTC CCT CCG AGG
Pro Val Ser Pro Pro Asn Glu Asp Ala Pro Pro Thr Leu Pro Pro Arg
    150                 155                 160

TCC GAT TCC CTC AAT AAG GTC ACT CCT CCC AAT CCT CCC AAT AAA GAC
Ser Asp Ser Leu Asn Lys Val Thr Pro Pro Asn Pro Pro Ile Lys Asp
165                 170                 175                 180

ACT CCG CAC ACA CCT CCA CCG CGG GAT TTC ACT ACT ATC CCT CCC CGA
Thr Pro His Thr Pro Pro Pro Arg Asp Phe Thr Thr Ile Pro Pro Arg
                185                 190                 195

TABLE 10-continued

DNA sequence (SEQ ID NO:5) of cDNA coding for Tc Ad ESA2
and the translated amino acid sequence (SEQ ID NO:6)

```
GCA GTT GCC AAT GAG AAA TCC ACC ACT AAA AAA GGG TTC CTA AGC AAG
Ala Val Ala Asn Glu Lys Ser Thr Thr Lys Lys Gly Phe Leu Ser Lys
            200                 205                 210

CTC AAT TGT TTC ACT TGT TTT TGATAACATT GTGCTGGCAC CAAAATTGAA
Leu Asn Cys Phe Thr Cys Phe
            215                 220

CTTGTTACAT TATTGAGAAT AAAGGTTTGC ATG
```

EXAMPLE 9
Expression of Tc Ad ESA1 (SEQ ID NO: 12) as a Tra T Fusion in *E. coli*

TraT is an outer membrane lipoprotein of certain strains of *E. coli*. We have cloned the gene coding for TraT obtained from the antibiotic resistance plasmid R100 (Ogata R. T. et al., 1982, J. Bact. 151 819–827) and have transferred this gene to a plasmid in which the expression of TraT is under the control of the leftward promoter ($P_L$) of the bacteriophage lambda. High levels of TraT can be obtained when the cells harbour the thermolabile repressor of $P_L$, $\lambda$cI857 (Remaut E et al 1980 Gene 15 81–93) are incubated at 38–42° C.

The gene coding for Tc Ad ESA1 has been fused to the 5' position of the coding region of TraT in such a way that the new gene codes for the first 30 amino acids of TraT (including the 20 amino acid long signal sequence) followed by some amino acids generated by restriction sites used for the DNA manipulations followed by the gene coding for Tc Ad ESA1 FIG. 1 and SEQ ID NOs. 28 and 29. Insertion into this position of the Tra-T gene (SEQ ID NO: 11) was made possible by the creation of a PvuII restriction site at codons 31 and 32 of the TraT gene by site directed mutagenesis. The Tc Ad ESA1 gene was obtained as a 570 bp XmnI (generated by cutting an EcoRI site, and filling with DNA polymerase I—Klenow fragment—and religating) to Hind III fragment.

In a suitable *E. coli* host, raising the temperature of a culture leads to the production of TraT-Tc Ad ESA1 fusion protein (SEQ ID NO: 29) of apparent molecular weight 22 kD at up to 50 mgs per litre per $OD_{600}$.

The signal sequence may be cleaved from the fusion product (as is normally the case when TraT is produced in *E. coli*) if the level of expression does not exceed the processing capacity of the cell and the terminal cysteine may be further modified. When producing this TraT-immunogen fusion (SEQ ID NO: 29) this modification may be advantageous as it may confer a self-adjuvanting character to the protein (International Patent Application PCT/AU87/00107 Title: Immunopotentiation).

Expression of TC Ad ESA4 (SEQ ID NO: 25) as a TraT Fusion

The gene coding for Tc Ad ESA4 (SEQ ID NO: 24) has been fused to the 5' portion of the coding region of TraT in a manner identical to the Tc Ad ESA1-TraT construct (SEQ ID NOs. 28 and 29). The whole of the coding region of Tc Ad ESA4 (95 amino acids) is expressed as a TraT Tc Ad ESA4 fusion under the control of the Lambda leftward promoter.

Cloning into PYETC114 and expression in Yeast

The cDNA fragment encoding Tc Ad ESA1 (SEQ ID NO: 11) was inserted into a yeast expression vector, pYEUC114, developed in the CSIRO Division of Biotechnology. This vector employs the Cup 1 gene (encoding metallothionine) of *Saccharomyces cerevisiae*. The accompanying promoter is inducible with copper when contained in yeast cells. The Cup 1 gene casette containing the copper-inducible Cup 1 promoter and a multi-cloning site is described in Australian Patent Application No. 15845/88 and in Macreadie et al, Plasmid 21, 147–150. The EcoR1 fragment containing the (previously described) Tc Ad ESA1 cDNA (SEQ ID NO: 11) was inserted into pYEUC114 replacing most of the Cup 1 coding sequence. This results in the synthesis of a fusion protein consisting of 4 amino acids from the N-terminus of metallothionine followed by the sequence shown in Table 6 and in (SEQ ID NO: 11). *Saccharomyces cerevisiae* cells (strain CL13-ABSY86, [α, ΔUra3 leu2 his pra1 prb1 prc1 cps1]) carrying the recombinant plasmid (pYEUC30B4E) were grown in minimal medium containing histidine and leucine. To induce expression of Tc Ad ESA1 (SEQ ID NO: 12), copper sulphate was added to the culture medium to 0.5 mM. After 2 hours in the presence of copper, the cells were harvested, treated with Zymolyase to remove the yeast outer cell wall and then examined by SDS-PAGE and western blotting. The recombinant plasmid containing Tc Ad ESA1 encoding DNA (SEQ ID NO: 12) was named pYEUC30B4E.

EXAMPLE 10
Purification of Recombinant Antigens from Bacteria and Yeast

The antigens expressed by recombinant *E. coli* cells can be purified for vaccination trials. By means of example the following is an illustration of how the Tc Ad ESA1 (SEQ ID NO: 12) is isolated.

Bacterial cells containing the recombinant plasmid described in Example 9 are grown in a suitable medium at 28° C. and the expression of Tc Ad ESA1 is induced by increasing the temperature to 42° C. and incubating the cultures at that temperature for 4–6 hours. Cells are recovered from cultures by centrifugation at 10,000×g for 10 mins at 4° C. The pellet is then resuspended in a suitable buffer such as 50 mM Tris-HCl, 10 mM EDTA, 50 mM NaCl, pH 8.0 and cells pelleted by centrifugation as before. The washed pellet is resuspended in a buffer such as 50 mM Tris-HCl, 1 mM EDTA, 5 mM DTT, 0.1 mM PMSF, pH 8.0 and homogenised in a Marton-Gaulin Homogeniser, 6 passes at 9000 psi. The cell homogenate is then centrifuged at 20,000×g for 20 min at 4° C. to collect the dense inclusion bodies which contain the recombinant antigen. The supernatant is decanted off and discarded and the pellet is resuspended in a solution suitable for solubilising the proteins in the inclusion bodies such as 8 M Urea, 100 mM NaPi, 1 mM EDTA, 40 mM DTT, pH 8.5 and incubated at 37° C. for 4 hours with stirring. The solubilised antigen can be recovered by passing the solution through a "Diaflo" Amicon YM30 membrane followed by concentration of the eluant on a "Diaflo" Amicon YM10 membrane. The retenate can then be adjusted to pH 3.0 by addition of phosphoric acid, diluted 1:1 with 8M Urea to reduce the Na$^+$ concentration to 50 mM and passed over a column of S-sepharose "Fast Flow" equilibrated with 8 M Urea, 50 mM NaPi, 5 mM EDTA, 5 mM DTT, pH 3.0. The recombinant antigen is eluted off the column with a 50–400 mM NaPi gradient. Fractions containing the 21 kD recombinant Tc Ad ESA1 antigen are pooled and concentrated on a "Diaflo" Amicon YM10 membrane. This concentrate is then made 0.1% with respect to SDS and dialysed in a 1000 D cut off dialysis sac against 8 M Urea, 50 mM NaPi, 2 mM DTT, 0.1% SDS, pH 8.5 to reduce the Na$^+$ concentration to 50 mM and increase the pH to 8.5. The antigen can then be dialysed against a solution containing 150 mM NaCl, 10 mM Tris-HCl, 0.006 mM Oxidised Glutathione, 0.06 mM Reduced Glutathione, 0.1% SDS, pH 8.5, at room temperature for 24 hours and finally against a solution containing 150 mM NaCl, 10 mM Tris-HCl, 0.1% SDS, pH 7.4, at room temperature for 24 hours. The antigen recovered from the dialysis sac can be sterilised by filtration through a 0.22 μm filter prior to formulation in a suitable adjuvant prior to vaccination of host animals.

A similar approach can be taken to purify the other recombinant antigens according to this specification although the details of the purification protocols will differ with each antigen.

Preparation of Recombinant Tc Ad ESA1 from Yeast

Yeast cells carrying pYEUC30B4E were grown for 2 days in minimal medium containing histidine and leucine. The cells were then placed in fresh medium, incubated for a further 2hrs and then copper sulphate was added to 0.5 mM. Incubations was-continued for a further 2 hrs whereupon the cells were harvested by centrifugation and lysed using the Braun cell homogenizer according to the manufacturer's instructions. Briefly the cells are broken by shaking with glass beads at high speed. The glass beads are allowed to settle out under gravity and the cell lysate collected. The crude lysate was centrifuged at 15,000 rpm and the resulting supernatant and pellet examined for the presence of Tc Ad ESA1 protein(SEQ ID NO: 12). The latter was found exclusively in the 15 krpm pellet. This pellet was subsequently dissolved in 50 mM ammonium bicarbonate solution containing 8M urea, 2% SDS, 10 mM EDTA and 2% mercaptoethanol. This crude material was then fractionated using a Sephadex G75 column run in 50 mM ammonium bicarbonate solution containing 1 mM EDTA, 0.1% SDS and 0.1% mercaptoethanol. Fractions containing material with the molecular weight expected of Tc Ad ESA1 (non-glycosylated) and reacting with an anti-serum (R45) raised in rabbits against Tc Ad ESA1 from adult parasites, were pooled and used in subsequent vaccination trials.

EXAMPLE 11
Host-Protection Using Recombinant Tc Ad ESA1 Produced by Yeast

| #295 | Worm numbers ± SD | % Protection |
|---|---|---|
| Controls | 413 ± 299 | |
| Vaccinates | 275 ± 166 | 33 |

Guinea pigs were vaccinated with a preparation of recombinant Tc Ad ESA1 and challenged with *T. colubriformis* as described above. It should be noted that the worm numbers in the control animals were uncharacteristically low and scattered in this particular experiment. In previous instances where this has occurred (see e.g. Table 3, Experiment 257) repeat experiments have resulted in increased levels of protection being observed (see e.g. Table 3, Experiment 236).

Recombinant bacteria were constructed which synthesize each of Tc Ad ESA 1–4 (SEQ 12, 6, 4, and 25, respectively). Standard molecular biology techniques were used in all cases. The details of the constructs varied slightly with each antigen but were similar in principle to that described in Example 10 for Tc Ad ESA1.

The recombinant antigens were purified from the recombinant bacteria essentially as described in Example 9 and used in vaccination and challenge trials against *T. colubriformis* as described for the native antigens in Example 2. Both sheep and guinea pigs have been used in these challenge experiments. All of the recombinant antigens have protected the vaccinated animals as measured by decreased worm burdens at slaughter and/or decreased egg output by vaccinated sheep as compared with non-vaccinated controls. Table 11 summarises the protection data obtained in these initial trials. Sheep were vaccinated intraperitoneally with the recombinant antigens in the presence of an immune stimulatory adjuvant. Two weeks after the second vaccination the sheep were challenged with *T. colubriformis* larvae. Post patency, faecal samples were taken each week to determine the number of eggs per g. Approximately 50 days after infection, the sheep were slaughtered, adult parasites recovered from the intestines and counted. % protection is compared with non-vaccinated control animals (the decrease in worm counts were very similar to the decreased faecal egg counts).

It is to be appreciated that the degree of protection can be reasonably expected to be improved by such parameters as optimising the dose of antigen, the adjuvant used, the vaccination route, the conformation of the antigen and/or by vaccinating animals with combinations of the antigens.

TABLE 11

| Recombinant antigen | TcAdESA1 | TcAdESA2 | TcAdESA3 | TcAdESA4 |
|---|---|---|---|---|
| % Protection in guinea pigs | 53 | 74 | 0 | 53 |
| % Protection in sheep | 23 | 46 | 35 | 23 |

EXAMPLE 12
Extension to Other Parasites

The Tc Ad ESA antigens produced by recombinant DNA technology are capable of inducing a protective immune response against *T. colubriformis* infestation in vaccinated animals. It is possible that this immune response may also provide protection against other species of parasitic nematodes such as those cited elsewhere in this specification, but it is more likely that the other species of parasitic nematodes express proteins which are related but not identical to the Tc Ad ESA antigens. For most species of parasitic nematodes, it is not practical to obtain sufficient parasite material to purify these components and identify their structure in preparation for cloning the gene from those parasites and testing the protective potential of the components. In these cases, the only means by which the related antigens can be tested is to use recombinant DNA methods to isolate the gene coding for the related proteins and to express the related proteins in recombinant organisms, purify the related proteins from those recombinant organisms and vaccinate animals-and challenge them with the other species of parasitic nematodes. Even in the cases where it is possible to obtain sufficient parasite material to purify antigens, the above approach using molecular biology to clone genes coding for protective antigens related to the Tc Ad ESA antigen genes is a preferable approach to developing vaccines. To demonstrate that this approach is feasible, the following example demonstrates that there are genes that are related to Tc Ad ESA1 and 4 (SEQ ID NOs. 11 and 24, respectively) in two species of parasitic nematodes other than *T. colubriformis*, namely *Haemonchus contortus* which is an abomasal parasite of sheep and goats in particular and *Dirofilaria immitis* which is a parasitise of dogs and cats. In addition, it is demonstrated that genes related to Tc Ad ESA2 (SEQ ID NO: 5) are present in *H. contortus. Ostertagia ostertaqi. Ostertagia circumcincta* and *D. immitis.*

Genomic DNA was purified from the various species of parasites by the method described by Herrmann and Frischauf 1987. 1 $\mu$g of each DNA preparation from *T. colubriformis, H. contortus.* and *D. immitis* was digested with each of the restriction enzymes BamHI, PstI and HindIII (Promega). In a separate experiment, 8 $\mu$g of each DNA preparation from *T. colubriformis. H. contortus. Ostertagia ostertagi, Ostertagia circumcincta* and *D. immitis* was digested with the restriction enzyme HinfI (Promega). The digested DNA together with appropriate size markers was electrophoresed in 0.4% agarose gels and 1.0% agarose gels to separate the DNA fragments according to their size. After staining the gels in ethidium bromide and photographing the DNA, the DNA in the gels was transferred to positively charged nylon membranes by alkaline transfer and the membranes prepared for hybridisation as recommended by the manufacturers (Amersham). Fragments of DNA coding for Tc Ad ESA1, 2 and 4 (SEQ ID NOs. 11, 5, and 24, respectively) were labeled with $^{32}$p by the random labeling method described in the kit sold by Boehringer-Manheim. The filters were then incubated for 20 hours at 42° C. and 16 hours at 55° C. in a solution of 5×SSPE, 5×Denhardts solution, 0.5% SDS and 20 $\mu$g/ml of denatured Herring sperm DNA (see Maniatis et al 1982) containing $10^6$ cpm/ml of the radioactive Tc Ad ESA DNA. The filters were then washed to remove any non-specifically bound DNA and exposed to X-ray film. Specific DNA sequences in both *H. contortus* and *D. immitis* DNA hybridized to the Tc Ad ESA1 and 4 DNA fragments (SEQ ID NOs. 11 and 24, respectively). Specific DNA sequences in *H. contortus. Ostertagia ostertagi, Ostertagia circumcincta* and *D. immitis hybridized to the Tc Ad ESA*2 DNA fragment (SEQ ID NO: 5). This demonstrates that these DNA sequences could be cloned from genomic DNA libraries or from cDNA libraries or prepared by other recombinant DNA techniques such as the polymerase chain reaction from these species of parasite and by extension from any other species of parasitic nematode and recombinant organisms could be constructed which synthesise these related genes for use in vaccines against the other species of parasitic nematodes.

EXAMPLE 13

Scale up of Manufacturing for Commercial Vaccines

The production and purification techniques so far described are carried out at laboratory scale. For commercial production of the antigens of the invention, large scale fermentation of transformed hosts is required.

The large scale fermentations are performed according to standard techniques, the particular techniques selected being appropriate to the transformed host used for production of the antigen.

INDUSTRIAL APPLICATIONS

The invention provides antigens which can be used as an effective vaccine for protection against parasitism of animals by parasitic nematodes, particularly *Trichostrongylus colubriformis* and *Haemonchus contortus.*

Antibodies raised against the purified antigens isolated from *Trichostrongylus colubriformis* and the DNA sequences coding for these proteins can be used to identify the related polypeptides and genes coding for the antigens from species of parasitic nematode other than *Trichostrongylus colubriformis*. The same DNA sequences and antibodies can be used to identify related antigens and genes coding for those proteins in a range of other species of nematode which are parasitic to man and domestic animals and it is anticipated that these proteins will provide effective vaccines against parasitism by those species of nematode whether isolated from the parasite itself or produced by recombinant DNA technology. Species of parasites and hosts they may infect include for example:

*Trichinella spiralis* or *Ancylostoma caninum* infections of man, *Strongylus vulgaris* infections of horses, *Trichostrongylus colubriformis* infections of sheep, *Haemonchus contortus* infections of goats, *Ostertagia ostertagi* infections of cattle, *Ascaris suum* or *Trichinella spiralis* infections of pigs, *Toxascaris leonina* or *Uncinaria stenocephala* infections of cats and *Ancylostoma caninum* or *Trichuris vulpis* infections of dogs as well as infections of the circulatory system of man by larvae of Toxocara sDD and of the circulatory system of dogs by *Dirofilaria immitis* as well as infections of the circulatory system, urogenital system, respiratory system, skin and subcutaneous tissues of these and other species of animal. It should be noted that this list is by no means complete.

REFERENCES

Adams, D B and Cobon, G S (1984) in *Reviews in Rural Science* Vol. 6 (Leng et al eds) National Library of Australia pp 67–74
Adams, D B (1989). *Int. J. Parasitol*, 19, 169–175.
Connan, R M (1965) Parasitology 55, p 10P.
Dineen, J K and Wagland B M (1982)—In "*Biology and Control of Endoparasites*" (Eds. L E A Symons, A D Donald and J K Dineen), Academic Press, pp 297–323.
Dineen, (1977) Int. J. Parasitol, 7, 211–215.
Donelson, J E, Bol Duke, D Moser, W Zeng, N E Erondu, R Lucius, A Renz, M Karam and G Z Flores (1988). *Mol. Biochem. Parasitol* 31, 241–250.
East, I J, Berrie D A and Fitzgerald D J, (1989) *Int. J. Parasitol.* 19, 271–274
Grandea, A G, Tuyen L K, Askikin N, Davis T B, Philip M, Cohen C and McReynolds L, (1989) *Mol. Biochem. Parasitol.* 35 31–42.
Hermann, B G and Frischauf A M (1987) in Methods in Enzymology 152 eds. Bergers and Kimmerl AR—Academic Press N.Y.
Hotez, P J, Le Trang N, McKerrow J H and Cerami A (1985). *J. Biol. Chem.* 260, 7343–7348.
Huynh, T V, Young R A and Davis R W, pp 49–78 in *DNA cloning* Vol. 1 (1985) ed Glover, D M.
King and Blakesley (1986)
Laemmli, U K (1970)—Nature (London) 227, 680–685.
Lucius, R., Erondu N, Kern A and Donelson JED (1988). *J. Exp. Med.* 168, 1199–1204.
Maniatis, T, Fritsch, E F and Sambrook, J (eds.) (1982). *Molecular Cloning: A laboratory manual*, CSH Laboratory, Cold Spring Harbor.
Macreadie, et al, (1989) *Plasmid* 21 147–150
McGillivery, D J, Yong W K, Riffkin G G and Adler B (1988) *Proc. Aust. Soc. Parasitol.* 45.
Munn, E A Greenwood B and Coadwell W J (1987), *Parasitology* 94 385–397.

Neilson, J T M (1975), *Int. J. Parasitol.* 5, 427–430

Neilson and Van de Walle, (1987) *Vet. Parasitol* 23. 211–221.

Nilsen, T W, Maroney P A, Goodwin R G, Perne K G, Denker J A, Nenduri J and Kazura J W (1988), *Proc. Natl. Acad. Sci US*, 85, 3604–3607.B O'Donnell, I J (1973)—*Aust. J. Biol. Sci.* 26, 401–413.

O'Donnell, I J, Dineen J K, Rothwell T L W and Marshall R C (1985)—*International Journal for Parasitology* 15, 29–136.

Rothwell, T L W, (1989). *Int. J. Parasitol.* 19, 139–168.

Rothwell, T L W, (1978)—*International Journal for Parasitology* 8, 33–37.

Rothwell, T L W, and Griffiths D. A. (1977)—*J of Parasitology* 63, 761–762.

Rothwell, T L W, and Love R.L . (1974)—*International Journal for Parasitology* 4, 293–299.

Sambrook J Fritsch E. F. and Manitis T. (1989) Molecular cloning—A Laboratory Manual 2nd Edition Cold Spring Harbor Laboratory, Cold Spring Harbour N.Y.

Sanger, F, Coulson A R, Barrell B G, Smith A J H and Roe B A (1980), *J. Mol. Biol.* 143, 161–178.

Savin, K W, Dopheide TAA, Frenkel M J, Grant W, Wagland B M and Ward C W, (1988) *Proc. Lorne Vaccines '88 meeting.*

Silberstein, D S and Despommier D D (1985)—*Science* 227, 948–950.

Stearne, P A, van Driel I R, Grego B, Simpson R J and Goding J W (1985)—*Journal of Immunology*, 134, 443–448.

Wallace, R B, Johnson P F, Tanaka S, Schold M, Itakura K and Abelson J (1980) *Science* 209, 1396–1400.

---

We claim:

1. An isolated polynucleotide segment comprising a nucleotide sequence encoding an excretory/secretory protein, obtainable from a parasitic stage of a parasitic nematode, wherein said excretory/secretory protein has a molecular weight selected from the group consisting of about 11 kD, about 17 kD, about 30 kD, about 37 kD and about 81 kD, as estimated by SDS-PAGE, wherein said protein confers protective immunity on a host against infection by a parasitic nematode, wherein said 11 kD protein comprises SEQ ID NO: 20, wherein said 17 kD protein comprises SEQ ID NO: 15, wherein said 30 kD protein comprises SEQ ID NO: 31, wherein said 37 kD protein comprises SEQ ID NO: 7, wherein said 81 kD protein comprises SEQ ID NO: 26.

2. A polynucleotide according to claim 1, wherein said protein is a 17 kD protein that comprises SEQ ID NO: 19.

3. A polynucleotide according to claim 2, wherein said 17 kD protein comprises SEQ ID NO: 4.

4. A polynucleotide according to claim 2, wherein said polynucleotide comprises SEQ ID NO: 18.

5. A polynucleotide according to claim 4, wherein said polynucleotide comprises SEQ ID NO: 3.

6. A polynucleotide according to claim 1, wherein said protein in an 11 kD protein that further comprises SEQ ID NO: 21.

7. A polynucleotide according to claim 6, wherein said 11 kD protein comprises SEQ ID NO: 25.

8. A polynucleotide according to claim 7, wherein said polynucleotide comprises SEQ ID NO: 24.

9. A polynucleotide according to claim 1, wherein said protein is a 30 kD protein that comprises SEQ ID NO: 31 and further comprises SEQ ID NOs. 1 and 2.

10. A polynucleotide according to claim 9, wherein said 30 kD protein comprises SEQ ID NO: 12.

11. A polynucleotide according to claim 10, wherein said polynucleotide comprises SEQ ID NO: 11.

12. A polynucleotide according to claim 1, wherein said protein is a 37 kD protein comprising SEQ ID NO: 6.

13. A polynucleotide according to claim 12, wherein said polynucleotide comprises SEQ ID NO: 5.

14. A polynucleotide according to claim 1, wherein said polynucleotide is a DNA molecule.

15. A polynucleotide according to claim 1, wherein said polynucleotide is a recombinant DNA molecule further comprising an expression control sequence operatively linked to said nucleotide sequence.

16. A polynucleotide molecule according to claim 15, wherein said expression control sequence is selected from the group consisting of the tryptophan operon, the leftward promoter of bacteriophage lambda, the tac promoter, the Cup 1 promoter and the SV40 early promoter.

17. An isolated host, comprising a host cell transformed with a polynucleotide according to claim 1.

18. An isolated host according to claim 17, wherein the host is a bacterial cell, a yeast or other fungus, a vertebrate cell, an insect cell, or a plant cell.

19. An isolated host cell according to claim 18, wherein the host is a human cell.

20. An isolated host cell according to claim 18, wherein the host cell is transformed with a vaccinia virus or a baculovirus.

21. An isolated host cell according to claim 18, wherein the host is *Saccharomyces cerevisiae*.

22. An isolated host cell according to claim 18, wherein the host cell is selected from the group consisting of *E. coli*, an enteric organism other than *E. coli*, a *Pseudomonas* and a *Bacillus species*.

23. An isolated host cell according to claim 22, wherein the host is an *E. coli* K12 cell selected from the group consisting of JM109 and Y1090.

24. An isolated host cell according to claim 22, wherein the host is *E. coli* strain BTA 1689 (ATCC 68099).

25. An isolated host cell according to claim 22, wherein the host is *E. coli* strain BTA 1691 (ATCC 68098).

26. An isolated host cell according to claim 22, wherein the host is *E. coli* strain BTA 1690 (ATCC 68100).

27. An isolated polynucleotide segment that encodes a fusion protein wherein said fusion protein comprises a protein encoded by a polynucleotide according to claim 15.

28. A polynucleotide segment according to claim 27, wherein said fusion protein comprises the *E. coli* β-galactosidase gene, the *E. coli* TraT gene, or the trp operon.

29. A method of preparing an expression product of a transformed host, comprising culturing a transformed host according to claim 17 and isolating an excretory/secretory protein of a parasitic stage of a nematode species, wherein said protein induces protective immunity against nematode infestation when administered to a vertebrate host.

* * * * *

SEQUENCE LISTING

```
(1) GENERAL INFORMATION:

(iii) NUMBER OF SEQUENCES: 32

(2) INFORMATION FOR SEQ ID NO:1:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (v) FRAGMENT TYPE: internal (vi) ORIGINAL SOURCE:
        (A) ORGANISM: Trichostrongylus colubriformis (xi) SEQUENCE DESCRIPTION: SEQ ID NO:1:

Lys Glu Gln Tyr Ser
1               5

(2) INFORMATION FOR SEQ ID NO:2:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (v) FRAGMENT TYPE: internal (vi) ORIGINAL SOURCE:
        (A) ORGANISM: Trichostrongylus colubriformis (xi) SEQUENCE DESCRIPTION: SEQ ID NO:2:

Lys Leu Ile Xaa Asp
1               5

(2) INFORMATION FOR SEQ ID NO:3:

(i) SEQUENCE CHARACTERISTICS:
        (A) LENGTH: 594 base pairs
        (B) TYPE: nucleic acid
        (C) STRANDEDNESS: double
        (D) TOPOLOGY: linear (ii) MOLECULE TYPE: cDNA to mRNA
```

(vi) ORIGINAL SOURCE:
    (A) ORGANISM: Trichostrongylus colubriformis (ix) FEATURE:
    (A) NAME/KEY: CDS
    (B) LOCATION: 1..519

(xi) SEQUENCE DESCRIPTION: SEQ ID NO:3:

```
ATG CGG TTC CTT CTT CTA GCA GCG TTC GTC GCC TAT GCG TAT GCA AAG        48
Met Arg Phe Leu Leu Leu Ala Ala Phe Val Ala Tyr Ala Tyr Ala Lys
 1               5                  10                  15

TCA GAT GAA GAA ATC CGA AAA GAT GCA CTA TCT GCT CTG GAT GTA GTT        96
Ser Asp Glu Glu Ile Arg Lys Asp Ala Leu Ser Ala Leu Asp Val Val
                20                  25                  30

CCA CTG GGT TCG ACT CCC GAA AAA CTG GAA AAT GGC AGG GAA TTC TAC       144
Pro Leu Gly Ser Thr Pro Glu Lys Leu Glu Asn Gly Arg Glu Phe Tyr
            35                  40                  45

AAA TAC TTC TTC ACC AAC CAT CAA GAT TTG CGC AAA TAC TTC AAG GGT       192
Lys Tyr Phe Phe Thr Asn His Gln Asp Leu Arg Lys Tyr Phe Lys Gly
50                  55                  60

GCC GAA ACT TTC ACT GCC GAT GAT ATC GCT AAG AGC GAC AGA TTC AAG       240
Ala Glu Thr Phe Thr Ala Asp Asp Ile Ala Lys Ser Asp Arg Phe Lys
 65                  70                  75                  80

AAA CTG GGC AAT CAG CTG CTT CTG TCA GTG CAT CTT GCC GCT GAC ACC       288
Lys Leu Gly Asn Gln Leu Leu Leu Ser Val His Leu Ala Ala Asp Thr
                85                  90                  95

TAC GAC AAC GAG ATG ATC TTC CGT GCA TTC GTC CGT GAT ACC ATC GAC       336
Tyr Asp Asn Glu Met Ile Phe Arg Ala Phe Val Arg Asp Thr Ile Asp
            100                 105                 110

CGA CAT GTC GAT CGT GGA CTT GAC CCC AAG CTG TGG AAG GAA TTC TGG       384
Arg His Val Asp Arg Gly Leu Asp Pro Lys Leu Trp Lys Glu Phe Trp
       115                 120                 125

AGC ATC TAC CAG AAA TTC TTG GAG AGC AAG GGA AAG ACA CTG AGC GCT       432
Ser Ile Tyr Gln Lys Phe Leu Glu Ser Lys Gly Lys Thr Leu Ser Ala
130                 135                 140

GAT CAG AAG GCT GCA TTT GAC GCC ATT GGC ACG CGA TTC AAC GAT GAG       480
Asp Gln Lys Ala Ala Phe Asp Ala Ile Gly Thr Arg Phe Asn Asp Glu
145                 150                 155                 160

GCT CAG AAA CAG CTT GCT CAC CAT GGA CTG CCA CAC ACA TAAGAAGTTT        529
Ala Gln Lys Gln Leu Ala His His Gly Leu Pro His Thr
                165                 170

GCTGAAAACT GTGCGAAGCT TGTGCATCT TTTTGCTCAA ATAAAGGTCG TTTAGGTAAA      589

AAAAA                                                                 594
```

(2) INFORMATION FOR SEQ ID NO:4:

(i) SEQUENCE CHARACTERISTICS:
        (A) LENGTH: 173 amino acids
        (B) TYPE: amino acid
        (D) TOPOLOGY: linear (ii) MOLECULE TYPE: protein (xi) SEQUENCE DESCRIPTION: SEQ ID NO:4:

```
Met Arg Phe Leu Leu Leu Ala Ala Phe Val Ala Tyr Ala Tyr Ala Lys
 1               5                  10                  15

Ser Asp Glu Glu Ile Arg Lys Asp Ala Leu Ser Ala Leu Asp Val Val
                20                  25                  30

Pro Leu Gly Ser Thr Pro Glu Lys Leu Glu Asn Gly Arg Glu Phe Tyr
            35                  40                  45

Lys Tyr Phe Phe Thr Asn His Gln Asp Leu Arg Lys Tyr Phe Lys Gly
       50                  55                  60
```

```
Ala Glu Thr Phe Thr Ala Asp Asp Ile Ala Lys Ser Asp Arg Phe Lys
 65                  70                  75                  80

Lys Leu Gly Asn Gln Leu Leu Leu Ser Val His Leu Ala Ala Asp Thr
                 85                  90                  95

Tyr Asp Asn Glu Met Ile Phe Arg Ala Phe Val Arg Asp Thr Ile Asp
            100                 105                 110

Arg His Val Asp Arg Gly Leu Asp Pro Lys Leu Trp Lys Glu Phe Trp
        115                 120                 125

Ser Ile Tyr Gln Lys Phe Leu Glu Ser Lys Gly Lys Thr Leu Ser Ala
130                 135                 140

Asp Gln Lys Ala Ala Phe Asp Ala Ile Gly Thr Arg Phe Asn Asp Glu
145                 150                 155                 160

Ala Gln Lys Gln Leu Ala His His Gly Leu Pro His Thr
                165                 170
```

(2) INFORMATION FOR SEQ ID NO:5:

(i) SEQUENCE CHARACTERISTICS:
        (A) LENGTH: 764 base pairs
        (B) TYPE: nucleic acid
        (C) STRANDEDNESS: double
        (D) TOPOLOGY: linear (ii) MOLECULE TYPE: cDNA to mRNA (vi) ORIGINAL SOURCE:
        (A) ORGANISM: Trichostrongylus colubriformis (ix) FEATURE:
        (A) NAME/KEY: CDS
        (B) LOCATION: 45..701

(xi) SEQUENCE DESCRIPTION: SEQ ID NO:5:

```
CCTGGTTGTT CCGCACTTTC ACTCGGCGCA GCTCTTCGAC GATG ATG CTG ATC CTT        56
                                              Met Leu Ile Leu
                                                1

CTG GCC ATT TTG GTC GGC ACC GTG CCT TCC GAG TCG TCG CTC GTA AAC       104
Leu Ala Ile Leu Val Gly Thr Val Pro Ser Glu Ser Ser Leu Val Asn
 5                  10                  15                  20

AGT GAC TAT AGG GTT CAC AAT GAC CAC TGT AAA TAC AGT GAG GTT AAG       152
Ser Asp Tyr Arg Val His Asn Asp His Cys Lys Tyr Ser Glu Val Lys
             25                  30                  35

CAG CAA CCG TTT AAA GAA ATC GCC AAC TCG TCA CTA CGA TCA TTC CTT       200
Gln Gln Pro Phe Lys Glu Ile Ala Asn Ser Ser Leu Arg Ser Phe Leu
         40                  45                  50

TTG AGA AAA CTG AGA GGG ATT GGG GAT ACT GAC TGC GTG CAG TCT TAC       248
Leu Arg Lys Leu Arg Gly Ile Gly Asp Thr Asp Cys Val Gln Ser Tyr
     55                  60                  65

CAA GTG GAG TTC AAC AAC GAC AGC AAT CCG TTT TAT GTC TTT CGC ATC       296
Gln Val Glu Phe Asn Asn Asp Ser Asn Pro Phe Tyr Val Phe Arg Ile
 70                  75                  80

GAC CGT GAG ACA AGA TTT TCA CGG AAC TAT ACC GTC TGC GGT GTG GTT       344
Asp Arg Glu Thr Arg Phe Ser Arg Asn Tyr Thr Val Cys Gly Val Val
 85                  90                  95                 100

ACT GTG GTT GGT GGC GAC TTC ATG TGG AAG TCA TGT GAT AAA TCG AAA       392
Thr Val Val Gly Gly Asp Phe Met Trp Lys Ser Cys Asp Lys Ser Lys
                105                 110                 115

TTC AAA GAC TAT CTT CTA AAG TGT GAG AGC GAA GAG AAC AGA CAT CCA       440
Phe Lys Asp Tyr Leu Leu Lys Cys Glu Ser Glu Glu Asn Arg His Pro
            120                 125                 130

CAA CTG CCA CCT GTT CTG TCA TGC GAC CGG ACC CCT AAT CCT GTC TCG       488
Gln Leu Pro Pro Val Leu Ser Cys Asp Arg Thr Pro Asn Pro Val Ser
```

|  |  |  |  |  |  |  |  |  |  |  |  |  |  |  |
|---|---|---|---|---|---|---|---|---|---|---|---|---|---|---|
|  | 135 |  |  |  | 140 |  |  |  |  | 145 |  |  |  |  |
| CCG | GTC | AGT | CCT | CCG | AAT | GAG | GAC | GCT | CCG | CCC | ACC | CTC | CCT | CCG | AGG | 536 |
| Pro | Val | Ser | Pro | Pro | Asn | Glu | Asp | Ala | Pro | Pro | Thr | Leu | Pro | Pro | Arg |
|  | 150 |  |  |  | 155 |  |  |  |  | 160 |  |  |  |  |
| TCC | GAT | TCC | CTC | AAT | AAG | GTC | ACT | CCT | CCC | AAT | CCT | CCC | ATT | AAA | GAC | 584 |
| Ser | Asp | Ser | Leu | Asn | Lys | Val | Thr | Pro | Pro | Asn | Pro | Pro | Ile | Lys | Asp |
| 165 |  |  |  | 170 |  |  |  |  | 175 |  |  |  |  | 180 |
| ACT | CCG | CAC | ACA | CCT | CCA | CCG | CGG | GAT | TTC | ACT | ACT | ATC | CCT | CCC | CGA | 632 |
| Thr | Pro | His | Thr | Pro | Pro | Pro | Arg | Asp | Phe | Thr | Thr | Ile | Pro | Pro | Arg |
|  |  |  |  | 185 |  |  |  |  | 190 |  |  |  |  | 195 |
| GCA | GTT | GCC | AAT | GAG | AAA | TCC | ACC | ACT | AAA | AAA | GGG | TTC | CTA | AGC | AAG | 680 |
| Ala | Val | Ala | Asn | Glu | Lys | Ser | Thr | Thr | Lys | Lys | Gly | Phe | Leu | Ser | Lys |
|  |  |  | 200 |  |  |  |  | 205 |  |  |  |  | 210 |  |
| CTC | AAT | TGT | TTC | ACT | TGT | TTT | TGATAACATT | GTGCTGGCAC | CAAAATTGAA |  |  |  |  |  |  | 731 |
| Leu | Asn | Cys | Phe | Thr | Cys | Phe |
|  |  | 215 |
| CCTGTTACAT | TATTGAGAAT | AAAGGTTTGC | ATG |  |  |  |  |  |  |  |  |  |  |  |  | 764 |

(2) INFORMATION FOR SEQ ID NO:6:

(i) SEQUENCE CHARACTERISTICS:
        (A) LENGTH: 219 amino acids
        (B) TYPE: amino acid
        (D) TOPOLOGY: linear (ii) MOLECULE TYPE: protein (xi) SEQUENCE DESCRIPTION: SEQ ID NO:6:

| Met | Leu | Ile | Leu | Leu | Ala | Ile | Leu | Val | Gly | Thr | Val | Pro | Ser | Glu | Ser |
|---|---|---|---|---|---|---|---|---|---|---|---|---|---|---|---|
| 1 |  |  |  | 5 |  |  |  |  | 10 |  |  |  |  | 15 |  |
| Ser | Leu | Val | Asn | Ser | Asp | Tyr | Arg | Val | His | Asn | Asp | His | Cys | Lys | Tyr |
|  |  |  | 20 |  |  |  |  | 25 |  |  |  |  | 30 |  |  |
| Ser | Glu | Val | Lys | Gln | Gln | Pro | Phe | Lys | Glu | Ile | Ala | Asn | Ser | Ser | Leu |
|  |  | 35 |  |  |  |  | 40 |  |  |  |  | 45 |  |  |  |
| Arg | Ser | Phe | Leu | Leu | Arg | Lys | Leu | Arg | Gly | Ile | Gly | Asp | Thr | Asp | Cys |
|  | 50 |  |  |  |  | 55 |  |  |  |  | 60 |  |  |  |  |
| Val | Gln | Ser | Tyr | Gln | Val | Glu | Phe | Asn | Asn | Asp | Ser | Asn | Pro | Phe | Tyr |
| 65 |  |  |  |  | 70 |  |  |  |  | 75 |  |  |  |  | 80 |
| Val | Phe | Arg | Ile | Asp | Arg | Glu | Thr | Arg | Phe | Ser | Arg | Asn | Tyr | Thr | Val |
|  |  |  |  | 85 |  |  |  |  | 90 |  |  |  |  | 95 |  |
| Cys | Gly | Val | Val | Thr | Val | Val | Gly | Gly | Asp | Phe | Met | Trp | Lys | Ser | Cys |
|  |  |  | 100 |  |  |  |  | 105 |  |  |  |  | 110 |  |  |
| Asp | Lys | Ser | Lys | Phe | Lys | Asp | Tyr | Leu | Leu | Lys | Cys | Glu | Ser | Glu | Glu |
|  |  | 115 |  |  |  |  | 120 |  |  |  |  | 125 |  |  |  |
| Asn | Arg | His | Pro | Gln | Leu | Pro | Pro | Val | Leu | Ser | Cys | Asp | Arg | Thr | Pro |
|  | 130 |  |  |  |  | 135 |  |  |  |  | 140 |  |  |  |  |
| Asn | Pro | Val | Ser | Pro | Val | Ser | Pro | Pro | Asn | Glu | Asp | Ala | Pro | Pro | Thr |
| 145 |  |  |  |  | 150 |  |  |  |  | 155 |  |  |  |  | 160 |
| Leu | Pro | Pro | Arg | Ser | Asp | Ser | Leu | Asn | Lys | Val | Thr | Pro | Pro | Asn | Pro |
|  |  |  | 165 |  |  |  |  | 170 |  |  |  |  | 175 |  |  |
| Pro | Ile | Lys | Asp | Thr | Pro | His | Thr | Pro | Pro | Pro | Arg | Asp | Phe | Thr | Thr |
|  |  |  | 180 |  |  |  |  | 185 |  |  |  |  | 190 |  |  |
| Ile | Pro | Pro | Arg | Ala | Val | Ala | Asn | Glu | Lys | Ser | Thr | Thr | Lys | Lys | Gly |
|  |  | 195 |  |  |  |  | 200 |  |  |  |  | 205 |  |  |  |
| Phe | Leu | Ser | Lys | Leu | Asn | Cys | Phe | Thr | Cys | Phe |  |  |  |  |  |
|  | 210 |  |  |  |  | 215 |  |  |  |  |  |  |  |  |  |

(2) INFORMATION FOR SEQ ID NO:7:

(i) SEQUENCE CHARACTERISTICS:
            (A) LENGTH: 13 amino acids
            (B) TYPE: amino acid
            (D) TOPOLOGY: linear (ii) MOLECULE TYPE: peptide (v) FRAGMENT TYPE: internal (vi) ORIGINAL SOURCE:
            (A) ORGANISM: Trichostrongylus colubriformis (xi) SEQUENCE DESCRIPTION: SEQ ID NO:7:

Lys Val Ile Pro Xaa Asn Pro Pro Ile Lys Asp Thr Pro
1               5                   10

(2) INFORMATION FOR SEQ ID NO:8:

(i) SEQUENCE CHARACTERISTICS:
            (A) LENGTH: 14 amino acids
            (B) TYPE: amino acid
            (D) TOPOLOGY: linear (ii) MOLECULE TYPE: peptide (v) FRAGMENT TYPE: N-terminal (vi) ORIGINAL SOURCE:
            (A) ORGANISM: Trichostrongylus colubriformis (xi) SEQUENCE DESCRIPTION: SEQ ID NO:8:

Lys Ser Asp Glu Glu Ile Ile Lys Asp Ala Leu Ser Ala Leu
1               5                   10

(2) INFORMATION FOR SEQ ID NO:9:

(i) SEQUENCE CHARACTERISTICS:
            (A) LENGTH: 7 amino acids
            (B) TYPE: amino acid
            (D) TOPOLOGY: linear (ii) MOLECULE TYPE: peptide (v) FRAGMENT TYPE: internal (vi) ORIGINAL SOURCE:
            (A) ORGANISM: Trichostrongylus colubriformis (xi) SEQUENCE DESCRIPTION: SEQ ID NO:9:

Asp Ile Glu Gln Leu Met Pro
1               5

(2) INFORMATION FOR SEQ ID NO:10:

(i) SEQUENCE CHARACTERISTICS:
            (A) LENGTH: 20 base pairs
            (B) TYPE: nucleic acid
            (C) STRANDEDNESS: double
            (D) TOPOLOGY: linear (vi) ORIGINAL SOURCE:
            (A) ORGANISM: Trichostrongylus colubriformis (ix) FEATURE:
            (A) NAME/KEY: modified_base
            (B) LOCATION: 6

(ix) FEATURE:
            (A) NAME/KEY: modified_base
            (B) LOCATION: 9

(ix) FEATURE:
            (A) NAME/KEY: modified_base (B) LOCATION: 12

(ix) FEATURE:
            (A) NAME/KEY: modified_base
            (B) LOCATION: 15

(ix) FEATURE:
            (A) NAME/KEY: modified_base
            (B) LOCATION: 18

(xi) SEQUENCE DESCRIPTION: SEQ ID NO:10:

GGCATVAGYT GYTCRATRTC                                               20

(2) INFORMATION FOR SEQ ID NO:11:

(i) SEQUENCE CHARACTERISTICS:
            (A) LENGTH: 507 base pairs
            (B) TYPE: nucleic acid
            (C) STRANDEDNESS: double
            (D) TOPOLOGY: linear (ii) MOLECULE TYPE: cDNA to mRNA (vi) ORIGINAL SOURCE:
            (A) ORGANISM: Trichostrongylus colubriformis (ix) FEATURE:
            (A) NAME/KEY: CDS
            (B) LOCATION: 25..414

(xi) SEQUENCE DESCRIPTION: SEQ ID NO:11:

GAATTCGGGG GCAACACTTA CAGT GCA AAC AAT AAG CAA CAG ACC GAC ATA        51
                          Ala Asn Asn Lys Gln Gln Thr Asp Ile
                           1               5

GAA CAA CTC ATG CCC AAA TAT AAC TCG ACG TTC GCG AAG ATG AAT GGA       99
Glu Gln Leu Met Pro Lys Tyr Asn Ser Thr Phe Ala Lys Met Asn Gly
 10              15                  20                  25

AAC TAT AGT TAT AAG CTG ATC TGG GAT GAC AGC ATG GTA TCT GAT GCG      147
Asn Tyr Ser Tyr Lys Leu Ile Trp Asp Asp Ser Met Val Ser Asp Ala
                 30                  35                  40

CTG CAA GAA GCA AAG GAG CAA TAC AGT ACG AAT GCT ACC TTC AAG ATC      195
Leu Gln Glu Ala Lys Glu Gln Tyr Ser Thr Asn Ala Thr Phe Lys Ile
             45                  50                  55

CGT CGG AGA AAG GTG TTC ATA AAG GGC GAT AAC GCA ACG ATG GAG GAA      243
Arg Arg Arg Lys Val Phe Ile Lys Gly Asp Asn Ala Thr Met Glu Glu
         60                  65                  70

AAA GTG GAG GGA GCT CTG AAG TAC CCC GTC TTG AGA GCC GAT AAA TTT      291
Lys Val Glu Gly Ala Leu Lys Tyr Pro Val Leu Arg Ala Asp Lys Phe
     75                  80                  85

CTT CGC CGT CTT CTC TGG TTC ACA CAC TAC GCA TGC AAT GGA TAT TAC      339
Leu Arg Arg Leu Leu Trp Phe Thr His Tyr Ala Cys Asn Gly Tyr Tyr
 90                  95                 100                 105

GAT ACG AAA GGT GGA CAC GAT GTC CTG ACT GTC GCG TGT CTC TAC AGA      387
Asp Thr Lys Gly Gly His Asp Val Leu Thr Val Ala Cys Leu Tyr Arg
                 110                 115                 120

GAG ATC GAT TAC AAA AAT TCT CAC TAT TAGAAAGCAG TCAACAAAAA           434
Glu Ile Asp Tyr Lys Asn Ser His Tyr
             125                 130

CAGCAGAGTA AACTGACTGC ACATTCCGC AGTTTTTGAA TAAATACTTG ATGCAACTCA    494

AAAAAAAAAA AAA                                                      507

(2) INFORMATION FOR SEQ ID NO:12:

(i) SEQUENCE CHARACTERISTICS:
            (A) LENGTH: 130 amino acids
            (B) TYPE: amino acid -continued (D) TOPOLOGY: linear (ii) MOLECULE TYPE: protein (xi) SEQUENCE DESCRIPTION: SEQ ID NO:12:

Ala Asn Asn Lys Gln Gln Thr Asp Ile Glu Gln Leu Met Pro Lys Tyr
 1               5                  10                  15

Asn Ser Thr Phe Ala Lys Met Asn Gly Asn Tyr Ser Tyr Lys Leu Ile
                20                  25                  30

Trp Asp Ser Met Val Ser Asp Ala Leu Gln Glu Ala Lys Glu Gln
            35                  40                  45

Tyr Ser Thr Asn Ala Thr Phe Lys Ile Arg Arg Lys Val Phe Ile
    50                  55                  60

Lys Gly Asp Asn Ala Thr Met Glu Glu Lys Val Glu Gly Ala Leu Lys
 65                  70                  75                  80

Tyr Pro Val Leu Arg Ala Asp Lys Phe Leu Arg Arg Leu Leu Trp Phe
                85                  90                  95

Thr His Tyr Ala Cys Asn Gly Tyr Tyr Asp Thr Lys Gly Gly His Asp
               100                 105                 110

Val Leu Thr Val Ala Cys Leu Tyr Arg Glu Ile Asp Tyr Lys Asn Ser
           115                 120                 125

His Tyr
   130

(2) INFORMATION FOR SEQ ID NO:13:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (v) FRAGMENT TYPE: internal (vi) ORIGINAL SOURCE:
        (A) ORGANISM: Trichostrongylus colubriformis (ix) FEATURE:
        (A) NAME/KEY: Modified-site
        (B) LOCATION: 5
        (D) OTHER INFORMATION: /note= "RESIDUE AT POSITION 5 MAY
            BE ASPARTIC ACID OR SERINE"

(xi) SEQUENCE DESCRIPTION: SEQ ID NO:13:

Glu Ile Ala Asp Xaa Ser Lys Arg
 1               5

(2) INFORMATION FOR SEQ ID NO:14:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (v) FRAGMENT TYPE: internal (vi) ORIGINAL SOURCE:
        (A) ORGANISM: Trichostrongylus colubriformis (xi) SEQUENCE DESCRIPTION: SEQ ID NO:14:

Asn Pro Pro Ile Lys Asp Thr Pro
 1               5

-continued (2) INFORMATION FOR SEQ ID NO:15:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (v) FRAGMENT TYPE: internal (vi) ORIGINAL SOURCE:
        (A) ORGANISM: Trichostrongylus colubriformis (xi) SEQUENCE DESCRIPTION: SEQ ID NO:15:

```
Lys Asp Ala Leu Ser Ala Leu Asp Val Val Pro Leu Gly Ser
1               5                   10
```

(2) INFORMATION FOR SEQ ID NO:16:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (v) FRAGMENT TYPE: internal (vi) ORIGINAL SOURCE:
        (A) ORGANISM: Trichostrongylus colubriformis (xi) SEQUENCE DESCRIPTION: SEQ ID NO:16:

```
Asp Glu Glu Ile Ile Lys Asp Ala
1               5
```

(2) INFORMATION FOR SEQ ID NO:17:

(i) SEQUENCE CHARACTERISTICS:
        (A) LENGTH: 23 base pairs
        (B) TYPE: nucleic acid
        (C) STRANDEDNESS: double
        (D) TOPOLOGY: linear (vi) ORIGINAL SOURCE:
        (A) ORGANISM: Trichostrongylus colubriformis (ix) FEATURE:
        (A) NAME/KEY: modified_base
        (B) LOCATION: 3

(ix) FEATURE:
        (A) NAME/KEY: modified_base
        (B) LOCATION: 6

(ix) FEATURE:
        (A) NAME/KEY: modified_base
        (B) LOCATION: 15

(ix) FEATURE:
        (A) NAME/KEY: modified_base
        (B) LOCATION: 18

(ix) FEATURE:
        (A) NAME/KEY: modified_base
        (B) LOCATION: 21

(xi) SEQUENCE DESCRIPTION: SEQ ID NO:17:

```
GCRTCYTTTA TTATYTCYTC RTC                                    23
```

(2) INFORMATION FOR SEQ ID NO:18:

(i) SEQUENCE CHARACTERISTICS:
        (A) LENGTH: 129 base pairs (B) TYPE: nucleic acid
(C) STRANDEDNESS: double
(D) TOPOLOGY: linear (ii) MOLECULE TYPE: cDNA to mRNA (vi) ORIGINAL SOURCE:
(A) ORGANISM: Trichostrongylus colubriformis (ix) FEATURE:
(A) NAME/KEY: CDS
(B) LOCATION: 1..129

(xi) SEQUENCE DESCRIPTION: SEQ ID NO:18:

```
CGG TTC CTT CTT CTA GCA GCG TTC GTC GCC TAT GCG TAT GCA AAG TCA       48
Arg Phe Leu Leu Leu Ala Ala Phe Val Ala Tyr Ala Tyr Ala Lys Ser
 1               5                  10                  15

GAT GAA GAA ATC CGA AAA GAT GCA CTA TCT GCT CTG GAT GTA GTT CCA       96
Asp Glu Glu Ile Arg Lys Asp Ala Leu Ser Ala Leu Asp Val Val Pro
                 20                  25                  30

CTG GGT TCG ACT CCC GAA AAA CTG GAA AAT GGC                          129
Leu Gly Ser Thr Pro Glu Lys Leu Glu Asn Gly
         35                  40
```

(2) INFORMATION FOR SEQ ID NO:19:

(i) SEQUENCE CHARACTERISTICS:
(A) LENGTH: 43 amino acids
(B) TYPE: amino acid
(D) TOPOLOGY: linear (ii) MOLECULE TYPE: protein (xi) SEQUENCE DESCRIPTION: SEQ ID NO:19:

```
Arg Phe Leu Leu Leu Ala Ala Phe Val Ala Tyr Ala Tyr Ala Lys Ser
 1               5                  10                  15

Asp Glu Glu Ile Arg Lys Asp Ala Leu Ser Ala Leu Asp Val Val Pro
                 20                  25                  30

Leu Gly Ser Thr Pro Glu Lys Leu Glu Asn Gly
         35                  40
```

(2) INFORMATION FOR SEQ ID NO:20:

(i) SEQUENCE CHARACTERISTICS:
(A) LENGTH: 9 amino acids
(B) TYPE: amino acid
(D) TOPOLOGY: linear (ii) MOLECULE TYPE: peptide (v) FRAGMENT TYPE: internal (vi) ORIGINAL SOURCE:
(A) ORGANISM: Trichostrongylus colubriformis (xi) SEQUENCE DESCRIPTION: SEQ ID NO:20:

```
Arg Leu Ala Asp Asp Ser Asp Phe Gly
1               5
```

(2) INFORMATION FOR SEQ ID NO:21:

(i) SEQUENCE CHARACTERISTICS:
(A) LENGTH: 11 amino acids
(B) TYPE: amino acid
(D) TOPOLOGY: linear (ii) MOLECULE TYPE: peptide (v) FRAGMENT TYPE: internal (vi) ORIGINAL SOURCE:
    (A) ORGANISM: Trichostrongylus colubriformis (xi) SEQUENCE DESCRIPTION: SEQ ID NO:21:

```
Asn Tyr Asp Trp Met Lys Gly Gln Trp Gln Asn
1               5                   10
```

(2) INFORMATION FOR SEQ ID NO:22:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (v) FRAGMENT TYPE: internal (vi) ORIGINAL SOURCE:
        (A) ORGANISM: Trichostrongylus colubriformis (xi) SEQUENCE DESCRIPTION: SEQ ID NO:22:

```
Trp Met Lys Gly Gln Trp Gln Asn
1               5
```

(2) INFORMATION FOR SEQ ID NO:23:

(i) SEQUENCE CHARACTERISTICS:
        (A) LENGTH: 23 base pairs
        (B) TYPE: nucleic acid
        (C) STRANDEDNESS: double
        (D) TOPOLOGY: linear (vi) ORIGINAL SOURCE:
        (A) ORGANISM: Trichostrongylus colubriformis (ix) FEATURE:
        (A) NAME/KEY: modified_base
        (B) LOCATION: 12
        (D) OTHER INFORMATION: /mod_base= i (xi) SEQUENCE DESCRIPTION: SEQ ID NO:23:

```
TTTTGCCATT GNCCTTTCAT CCA                                      23
```

(2) INFORMATION FOR SEQ ID NO:24:

(i) SEQUENCE CHARACTERISTICS:
        (A) LENGTH: 461 base pairs
        (B) TYPE: nucleic acid
        (C) STRANDEDNESS: double
        (D) TOPOLOGY: linear (ii) MOLECULE TYPE: cDNA to mRNA (vi) ORIGINAL SOURCE:
        (A) ORGANISM: Trichostrongylus colubriformis (ix) FEATURE:
        (A) NAME/KEY: CDS
        (B) LOCATION: 72..356

(xi) SEQUENCE DESCRIPTION: SEQ ID NO:24:

```
TACAAGACCC CCAATTGTAC ACGAAATTCT TCAACGAAGA AAACAGCCTA AATCTGAGAT    60

GGAACCCACA T ATG TCG CAG CAT GCT CTA CAA GAA ATT GAG AAG CCA GGG   110
             Met Ser Gln His Ala Leu Gln Glu Ile Glu Lys Pro Gly
             1               5                   10

AAA TTT TCG CAA AAA GAT TCA GCA TAT TTC AAG CTC GAA AAC AAG AGG    158
Lys Phe Ser Gln Lys Asp Ser Ala Tyr Phe Lys Leu Glu Asn Lys Arg
    15                  20                  25

GAA CTG AAG GGA GAC AAT CTA CCA GTG GAG GAG AAA GTA CGC CAA ACT    206
```

```
Glu Leu Lys Gly Asp Asn Leu Pro Val Glu Glu Lys Val Arg Gln Thr
 30                      35                      40                      45

ATT GAA AAA TTC AAG GAT GAT GTA AGC GAA ATC AGA CGT CTC GCT GAT       254
Ile Glu Lys Phe Lys Asp Asp Val Ser Glu Ile Arg Arg Leu Ala Asp
                     50                      55                      60

GAT TCG GAT TTT GGA TGC AAC GGC AAA GAA ACC GAG GGT GCA ATG CAC       302
Asp Ser Asp Phe Gly Cys Asn Gly Lys Glu Thr Glu Gly Ala Met His
             65                      70                      75

ATT GTG TGT TTC TTC CAG AAG AAT TAT GAC TGG ATG AAA GGA CAA TGG       350
Ile Val Cys Phe Phe Gln Lys Asn Tyr Asp Trp Met Lys Gly Gln Trp
                     80                      85                      90

CAA AAC TGATTTTTCT GAAGTACTTG TTGGATTCTT CGTAGAATCG ATGCACAAAA        406
Gln Asn
     95

TACCTTTTTT GGGAGACAAC TTCGCATAAA ACTTCTCGAT GAAAAAAAAA AAAAA          461
```

(2) INFORMATION FOR SEQ ID NO:25:

(i) SEQUENCE CHARACTERISTICS:
        (A) LENGTH: 95 amino acids
        (B) TYPE: amino acid
        (D) TOPOLOGY: linear (ii) MOLECULE TYPE: protein (xi) SEQUENCE DESCRIPTION: SEQ ID NO:25:

```
Met Ser Gln His Ala Leu Gln Glu Ile Glu Lys Pro Gly Lys Phe Ser
 1               5                      10                      15

Gln Lys Asp Ser Ala Tyr Phe Lys Leu Glu Asn Lys Arg Glu Leu Lys
             20                      25                      30

Gly Asp Asn Leu Pro Val Glu Glu Lys Val Arg Gln Thr Ile Glu Lys
         35                      40                      45

Phe Lys Asp Asp Val Ser Glu Ile Arg Arg Leu Ala Asp Asp Ser Asp
     50                      55                      60

Phe Gly Cys Asn Gly Lys Glu Thr Glu Gly Ala Met His Ile Val Cys
 65                      70                      75                      80

Phe Phe Gln Lys Asn Tyr Asp Trp Met Lys Gly Gln Trp Gln Asn
             85                      90                      95
```

(2) INFORMATION FOR SEQ ID NO:26:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (v) FRAGMENT TYPE: N-terminal (vi) ORIGINAL SOURCE:
        (A) ORGANISM: Trichostrongylus colubriformis (xi) SEQUENCE DESCRIPTION: SEQ ID NO:26:

```
Ser Xaa Ser Leu Lys Asp
 1               5
```

(2) INFORMATION FOR SEQ ID NO:27:

(i) SEQUENCE CHARACTERISTICS:
        (A) LENGTH: 18 base pairs
        (B) TYPE: nucleic acid
        (C) STRANDEDNESS: double
        (D) TOPOLOGY: linear (vi) ORIGINAL SOURCE:
                 (A) ORGANISM: Trichostrongylus colubriformis (ix) FEATURE:
                (A) NAME/KEY: modified_base
                (B) LOCATION: 1

(ix) FEATURE:
                (A) NAME/KEY: modified_base
                (B) LOCATION: 4

(ix) FEATURE:
                (A) NAME/KEY: modified_base
                (B) LOCATION: 7
                (D) OTHER INFORMATION: /mod_base= i (ix) FEATURE:
                (A) NAME/KEY: modified_base
                (B) LOCATION: 10
                (D) OTHER INFORMATION: /mod_base= i (ix) FEATURE:
                (A) NAME/KEY: modified_base
                (B) LOCATION: 13..16
                (D) OTHER INFORMATION: /mod_base= i (xi) SEQUENCE DESCRIPTION: SEQ ID NO:27:

```
RTCYTTNARN GANNNNGA                                                18
```

(2) INFORMATION FOR SEQ ID NO:28:

(i) SEQUENCE CHARACTERISTICS:
                (A) LENGTH: 150 base pairs
                (B) TYPE: nucleic acid
                (C) STRANDEDNESS: double
                (D) TOPOLOGY: linear (ix) FEATURE:
                (A) NAME/KEY: CDS
                (B) LOCATION: 1..150

(ix) FEATURE:
                (A) NAME/KEY: misc_signal
                (B) LOCATION: 1..60

(ix) FEATURE:
                (A) NAME/KEY: misc_signal
                (B) LOCATION: 118..132

(ix) FEATURE:
                (A) NAME/KEY: misc_feature
                (B) LOCATION: 61..90
                (D) OTHER INFORMATION: /standard_name= "TraT N-Terminus"

(ix) FEATURE:
                (A) NAME/KEY: misc_feature
                (B) LOCATION: 91..117

(ix) FEATURE:
                (A) NAME/KEY: mat_peptide
                (B) LOCATION: 133..150

(xi) SEQUENCE DESCRIPTION: SEQ ID NO:28:

```
ATG AAA ATG AAA AAA TTG ATG ATG GTT GCA CTG GTC AGT TCC ACT CTG       48
Met Lys Met Lys Lys Leu Met Met Val Ala Leu Val Ser Ser Thr Leu
-44             -40                 -35                 -30

GCC CTT TCA GGG TGT GGT GCG ATG AGC ACA GCA ATC AAG AAG CAG AAT       96
Ala Leu Ser Gly Cys Gly Ala Met Ser Thr Ala Ile Lys Lys Gln Asn
        -25                 -20                 -15

TCG AGC TCG GTA CAA TTC GGG GGC AAC ACT TAC AGT GCA AAC AAT AAG      144
Ser Ser Ser Val Gln Phe Gly Gly Asn Thr Tyr Ser Ala Asn Asn Lys
            -10                 -5                   1

CAA CAG                                                              150
Gln Gln
```

(2) INFORMATION FOR SEQ ID NO:29:

(i) SEQUENCE CHARACTERISTICS:
        (A) LENGTH: 50 amino acids
        (B) TYPE: amino acid
        (D) TOPOLOGY: linear (ii) MOLECULE TYPE: protein (xi) SEQUENCE DESCRIPTION: SEQ ID NO:29:

```
Met Lys Met Lys Lys Leu Met Met Val Ala Leu Val Ser Ser Thr Leu
-44             -40             -35             -30

Ala Leu Ser Gly Cys Gly Ala Met Ser Thr Ala Ile Lys Lys Gln Asn
        -25             -20             -15

Ser Ser Ser Val Gln Phe Gly Gly Asn Thr Tyr Ser Ala Asn Asn Lys
    -10              -5               1

Gln Gln
  5
```

(2) INFORMATION FOR SEQ ID NO:30:

(i) SEQUENCE CHARACTERISTICS:
        (A) LENGTH: 23 base pairs
        (B) TYPE: nucleic acid
        (C) STRANDEDNESS: double
        (D) TOPOLOGY: linear (ix) FEATURE:
        (A) NAME/KEY: modified_base
        (B) LOCATION: 3
        (D) OTHER INFORMATION: /mod_base= i (ix) FEATURE:
        (A) NAME/KEY: modified_base
        (B) LOCATION: 12
        (D) OTHER INFORMATION: /mod_base= i (ix) FEATURE:
        (A) NAME/KEY: modified_base
        (B) LOCATION: 15
        (D) OTHER INFORMATION: /mod_base= i (ix) FEATURE:
        (A) NAME/KEY: modified_base
        (B) LOCATION: 18
        (D) OTHER INFORMATION: /mod_base= i (xi) SEQUENCE DESCRIPTION: SEQ ID NO:30:

GGNGTATCTT TNATNGGNGG ATT                      23

(2) INFORMATION FOR SEQ ID NO:31:

(i) SEQUENCE CHARACTERISTICS:
        (A) LENGTH: 16 amino acids
        (B) TYPE: amino acid
        (D) TOPOLOGY: linear (ii) MOLECULE TYPE: peptide (v) FRAGMENT TYPE: N-terminal (vi) ORIGINAL SOURCE:
        (A) ORGANISM: Trichostrongylus colubriformis (xi) SEQUENCE DESCRIPTION: SEQ ID NO:31:

```
Ala Asn Asn Lys Xaa Gln Xaa Asp Ile Glu Gln Leu Met Pro Lys Tyr
1               5                   10                  15
```

-continued

```
(2) INFORMATION FOR SEQ ID NO:32:

(i) SEQUENCE CHARACTERISTICS:
        (A) LENGTH: 23 base pairs
        (B) TYPE: nucleic acid
        (C) STRANDEDNESS: double
        (D) TOPOLOGY: linear (vi) ORIGINAL SOURCE:
        (A) ORGANISM: Trichostrongylus colubriformis (ix) FEATURE:
        (A) NAME/KEY: modified_base
        (B) LOCATION: 3

(ix) FEATURE:
        (A) NAME/KEY: modified_base
        (B) LOCATION: 6

(ix) FEATURE:
        (A) NAME/KEY: modified_base
        (B) LOCATION: 9

(ix) FEATURE:
        (A) NAME/KEY: modified_base
        (B) LOCATION: 12

(ix) FEATURE:
        (A) NAME/KEY: modified_base
        (B) LOCATION: 15

(ix) FEATURE:
        (A) NAME/KEY: modified_base
        (B) LOCATION: 18
        (D) OTHER INFORMATION: /mod_base= i (ix) FEATURE:
        (A) NAME/KEY: modified_base
        (B) LOCATION: 21

(xi) SEQUENCE DESCRIPTION: SEQ ID NO:32:

GGNGTRTCYT TNATNGGNGG RTT                                                    23
```